United States Patent
Jansen

(10) Patent No.: US 9,622,759 B2
(45) Date of Patent: Apr. 18, 2017

(54) SPLINE ORIENTED INDEXING GUIDE

(75) Inventor: David R. Jansen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 641 days.

(21) Appl. No.: 13/447,407

(22) Filed: Apr. 16, 2012

(65) Prior Publication Data

US 2012/0271312 A1    Oct. 25, 2012

Related U.S. Application Data

(60) Provisional application No. 61/477,800, filed on Apr. 21, 2011.

(51) Int. Cl.
| | | |
|---|---|---|
| *A61B 17/16* | (2006.01) | |
| *A61B 17/17* | (2006.01) | |
| *A61F 2/46* | (2006.01) | |
| *A61F 2/44* | (2006.01) | |
| *A61F 2/30* | (2006.01) | |
| *A61B 90/00* | (2016.01) | |

(52) U.S. Cl.
CPC ...... *A61B 17/1671* (2013.01); *A61B 17/1604* (2013.01); *A61B 17/1757* (2013.01); *A61F 2/4425* (2013.01); *A61F 2/4611* (2013.01); *A61F 2/4684* (2013.01); *A61B 2090/034* (2016.02); *A61F 2002/3082* (2013.01); *A61F 2002/30324* (2013.01); *A61F 2002/30805* (2013.01); *A61F 2002/30848* (2013.01); *A61F 2002/30878* (2013.01); *A61F 2002/30884* (2013.01); *A61F 2002/443* (2013.01)

(58) Field of Classification Search
CPC . A61B 17/17; A61B 17/1732; A61B 17/1739; A61B 17/1757; A61F 2/46; A61F 2/4603; A61F 2/4611; A61F 2/44; A61F 2/442; A61F 2/4455; A61F 2002/4623; A61F 2002/4624; A61F 2002/4625; A61F 2002/4629; A61F 2002/4635; A61F 2002/30878
USPC ................. 606/79, 80, 86 A, 87, 96, 99, 914
See application file for complete search history.

(56) References Cited

U.S. PATENT DOCUMENTS 5,423,826 A * 6/1995 Coates et al. ................. 606/96
6,159,214 A * 12/2000 Michelson ........... A61B 17/025
606/80

(Continued)

FOREIGN PATENT DOCUMENTS

WO    WO 2008/064211    5/2008

*Primary Examiner* — Kevin T Truong
*Assistant Examiner* — Tracy Kamikawa
(74) *Attorney, Agent, or Firm* — Baker & Hostetler LLP

(57) ABSTRACT

A surgical cutting system can be configured to prepare an intervertebral space for insertion of an intervertebral implant. In an embodiment, the surgical cutting system includes a drill guide and a drill bit. The drill guide can be configured to be coupled to a trial implant and can include a guide portion that is configured to support a first stop member. In addition, the drill guide defines a guide hole that extends through the guide portion along a guide hole axis. The drill bit can be configured to be at least partially received in the guide hole. Moreover, the drill bit defines a second stop member that is configured abut the first stop member so as to limit movement of the drill bit through the guide hole along the guide hole axis to a maximum cut depth.

25 Claims, 16 Drawing Sheets

(56) References Cited

U.S. PATENT DOCUMENTS

| | | | |
|---|---|---|---|
| 6,524,312 B2* | 2/2003 | Landry | A61B 17/1757 |
| | | | 606/279 |
| 6,936,071 B1 | 8/2005 | Marnay et al. | |
| 7,083,623 B2* | 8/2006 | Michelson | 606/80 |
| 7,083,625 B2* | 8/2006 | Berry | A61B 17/1757 |
| | | | 606/80 |
| 7,141,074 B2 | 11/2006 | Fanger et al. | |
| 7,491,204 B2 | 2/2009 | Marnay et al. | |
| 2006/0084986 A1* | 4/2006 | Grinberg et al. | 606/61 |
| 2006/0095044 A1* | 5/2006 | Grady et al. | 606/96 |
| 2007/0118224 A1* | 5/2007 | Shah et al. | 623/17.15 |
| 2008/0234684 A1* | 9/2008 | Gil et al. | 606/87 |
| 2008/0264109 A1* | 10/2008 | Ritchey | A61B 17/1725 |
| | | | 66/88 |
| 2010/0004657 A1* | 1/2010 | Dudasik | 606/96 |

* cited by examiner

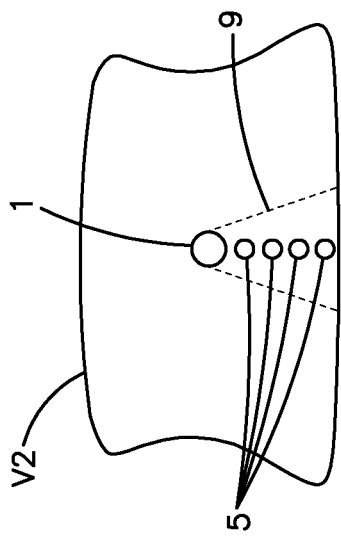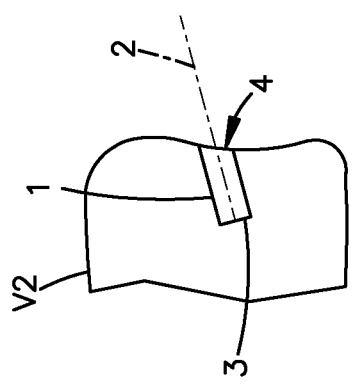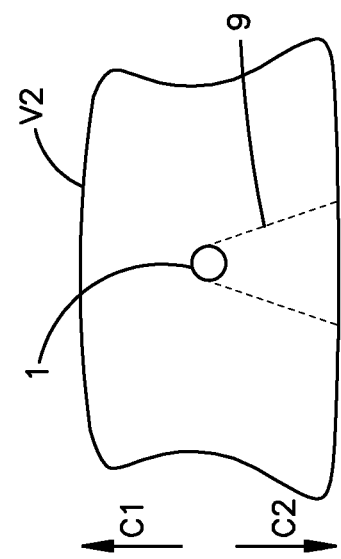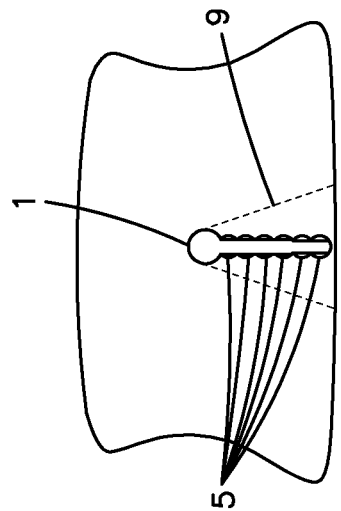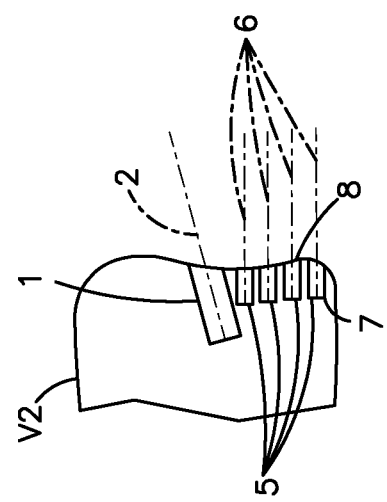

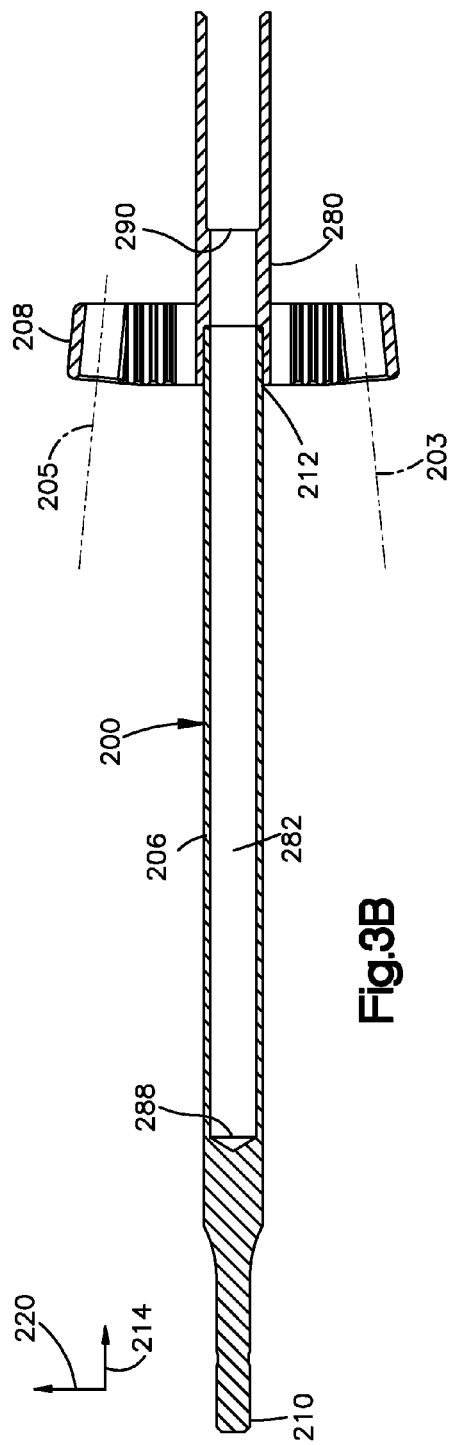
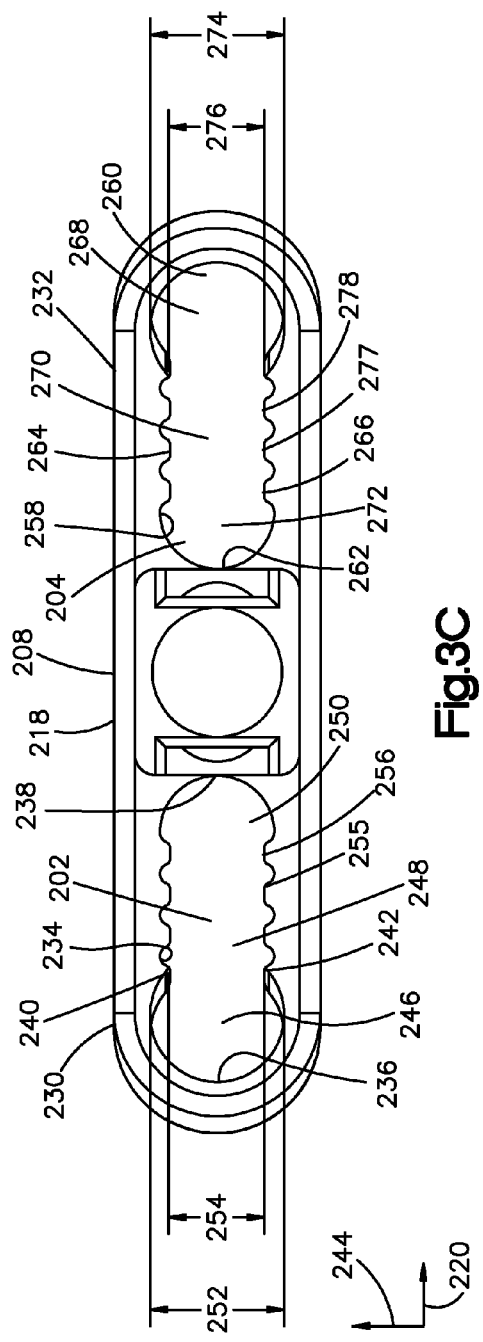
Fig.3B
Fig.3C

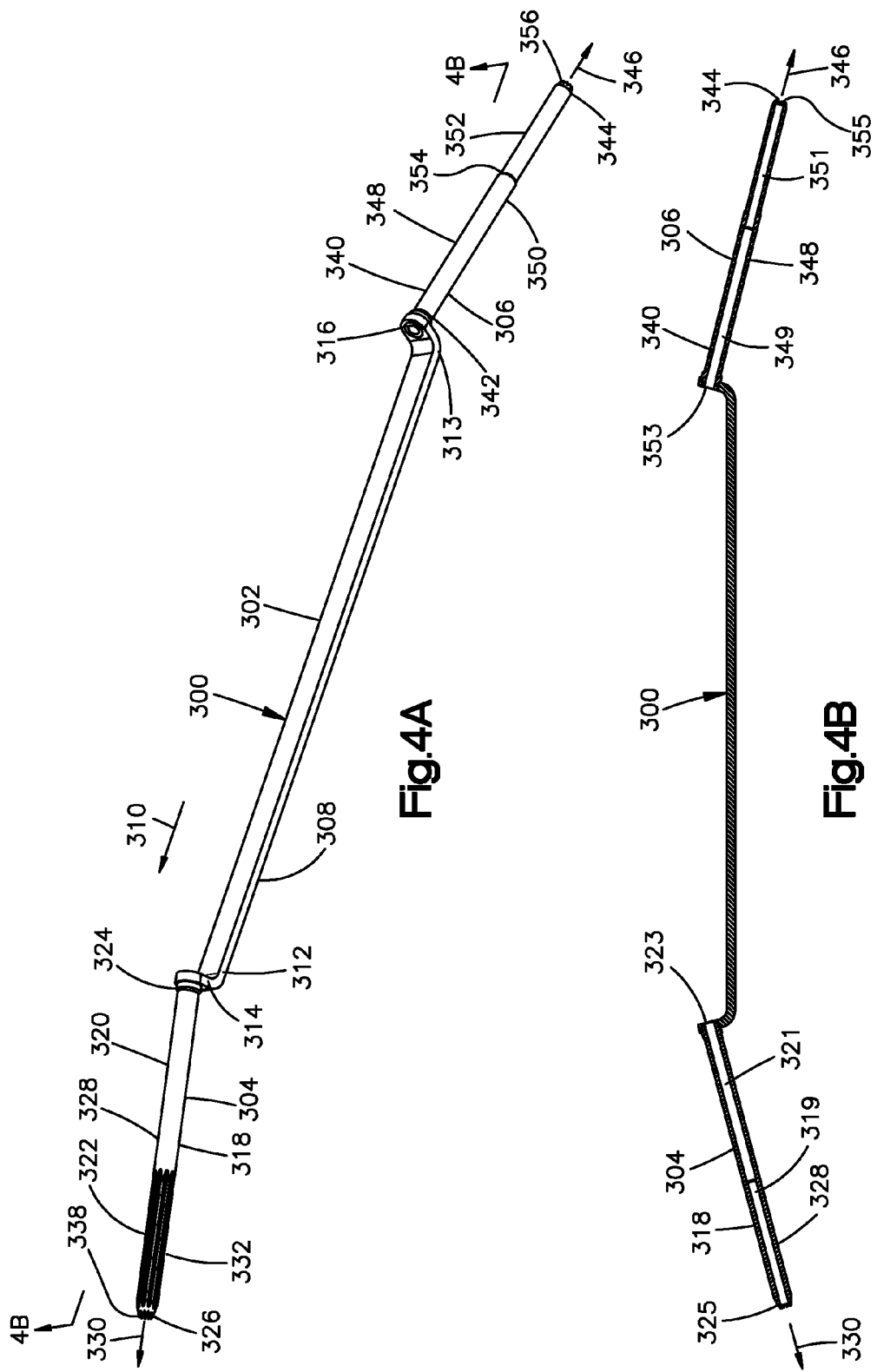

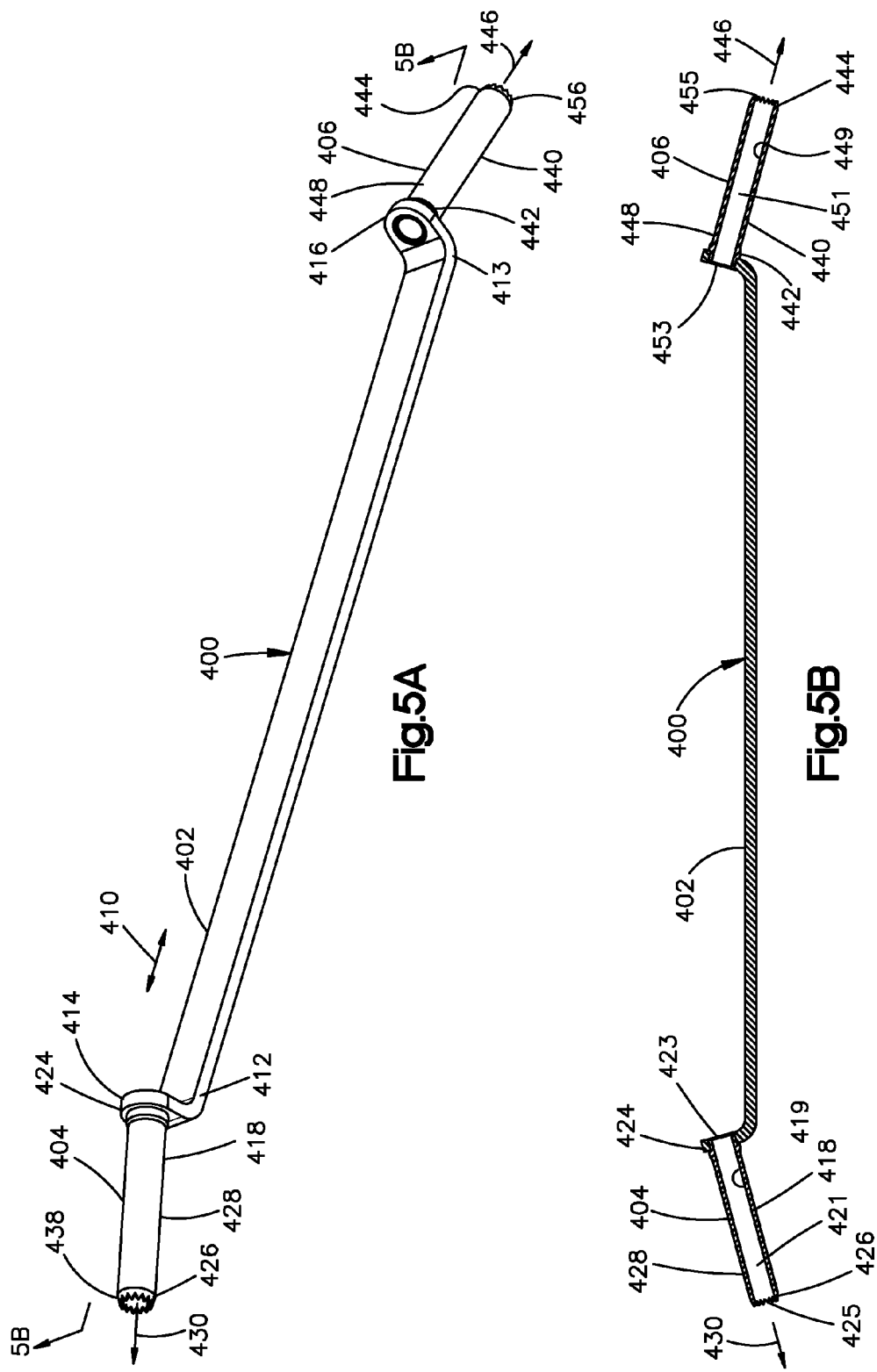

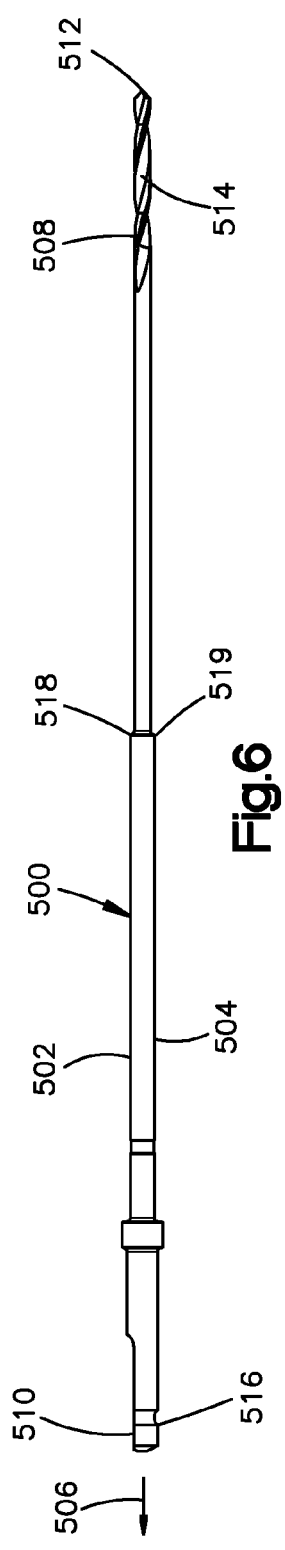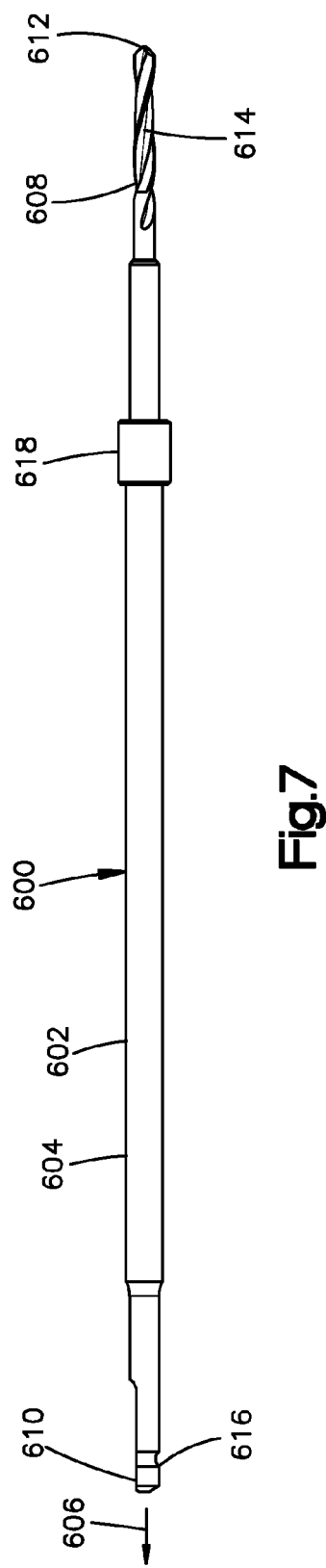
Fig.6
Fig.7

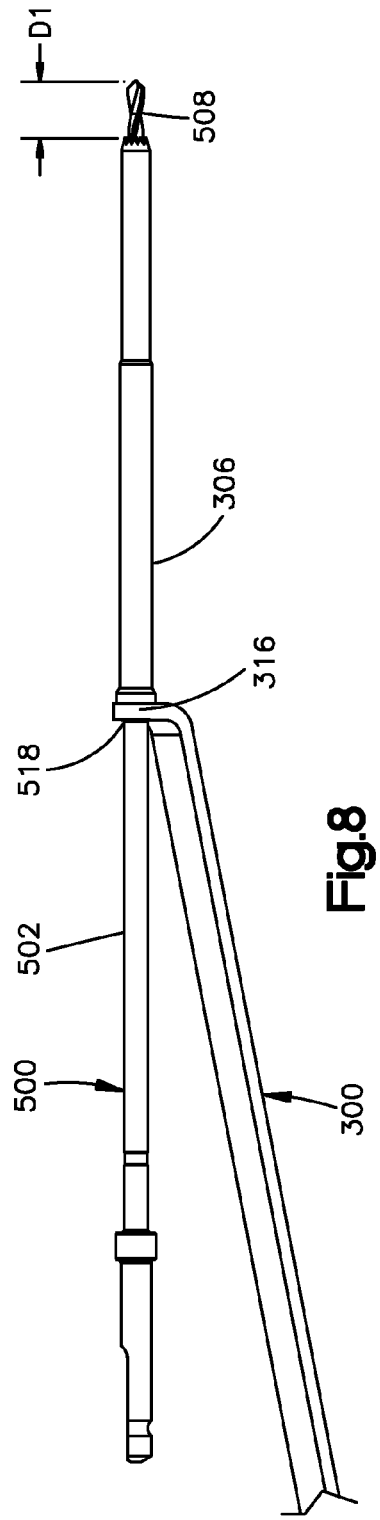
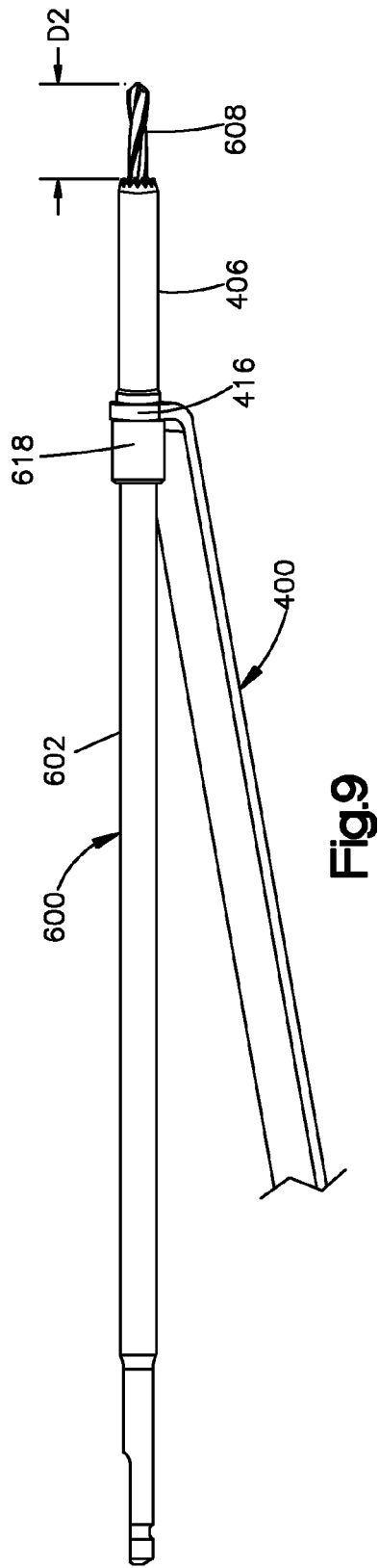

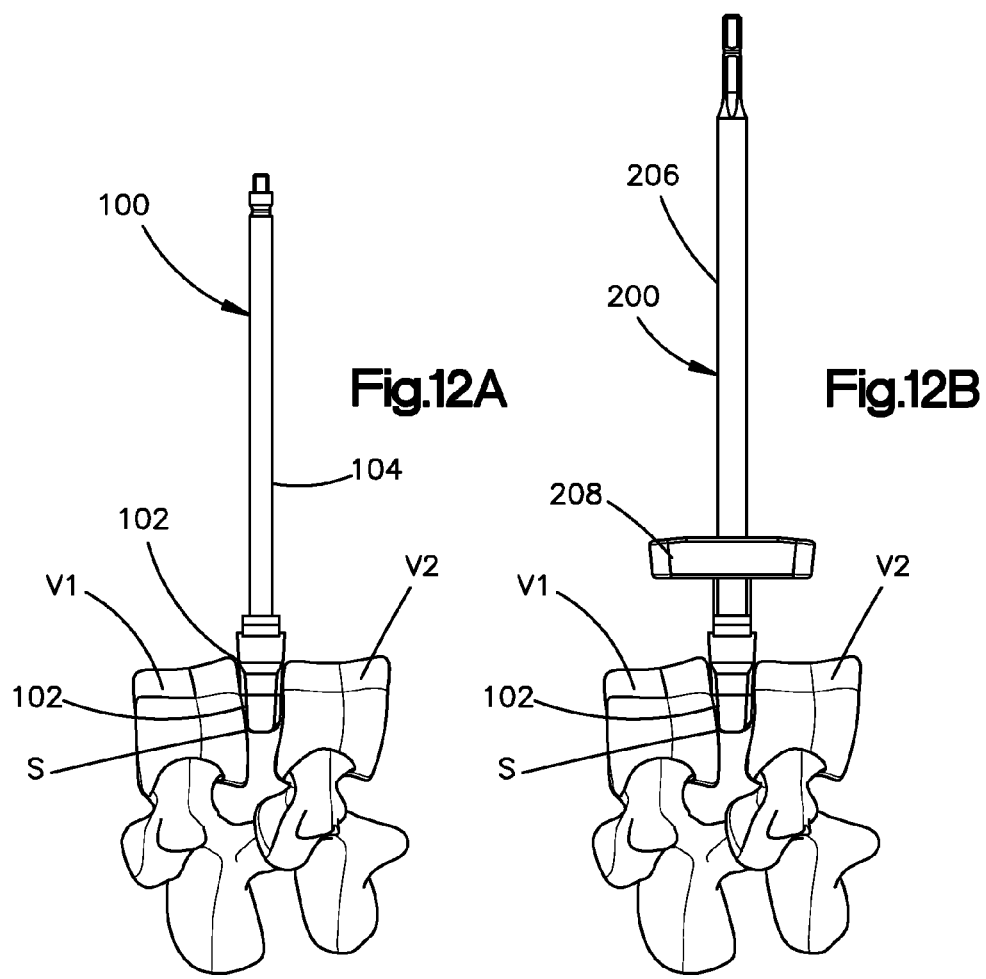

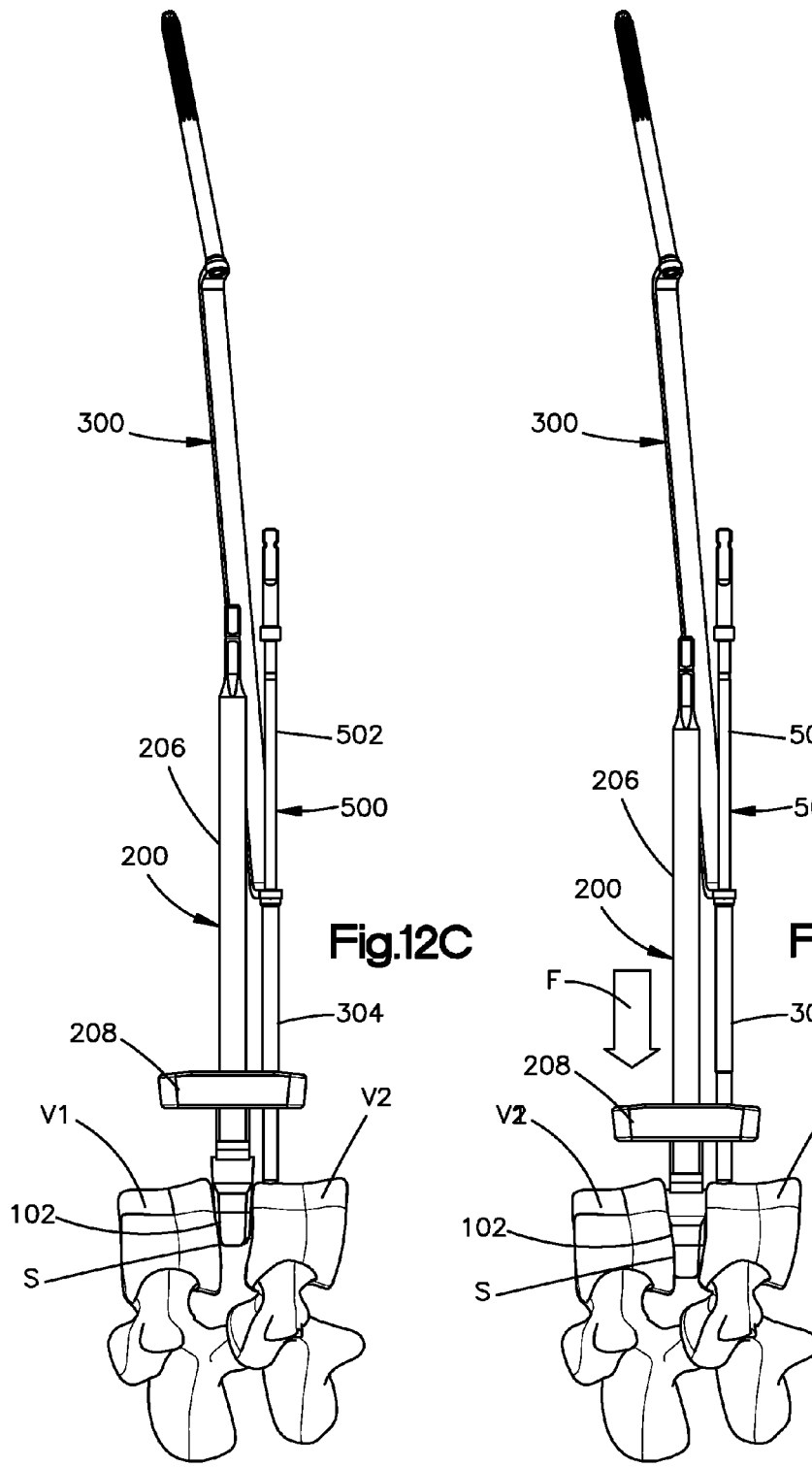

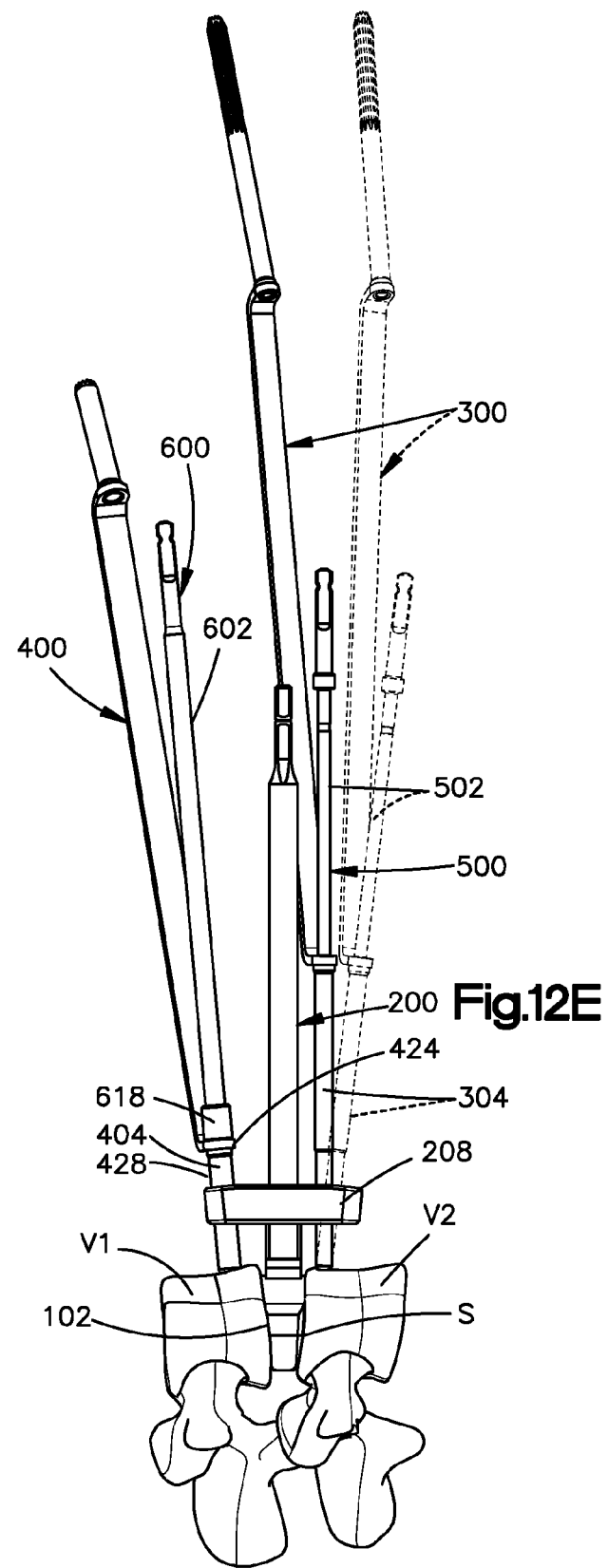

SPLINE ORIENTED INDEXING GUIDE

CROSS-REFERENCE TO RELATED APPLICATION

This application claims the benefit of U.S. Provisional Application No. 61/477,800, filed on Apr. 21, 2011, the entire disclosure of which is herein incorporated by reference.

TECHNICAL FIELD

The present application relates generally to methods and instruments for drilling multiple holes that are close together. More specifically the application discloses methods and instruments for maintaining a desired radial location and axial alignment of a drill bit while drilling overlapping holes in bone.

BACKGROUND

In orthopedic surgery, drill bits have a tendency to skip or slide along the surface of a bone instead of boring into the bone as desired. This skipping or sliding is known as skiving. Skiving can alter the intended trajectory or position of a hole that is drilled into the bone. A drill guide can be used in some situations to help control the radial location and axial alignment of a drill bit. However, drill guides are typically limited to a single location and orientation to a desired datum.

During certain orthopedic surgery procedures a channel is cut into a bone. For example, during a spinal disc replacement procedure a channel can be cut into a vertebra of a spinal column. The channel is configured to receive an anchoring structure of an implant, such as a keel, to secure the implant within the spinal column. In softer bone, for example cervical vertebral bodies, a side-cutting drill can be used in a sweeping fashion to remove a channel of bone. In harder sclerotic bone, as is often found in the lumbar of the spine, the use or effectiveness of a side-cutting drill bit may be limited. Where a side-cutting drill bit cannot be used, a series of partially overlapping, in-line drill holes may be used to approximate the channel cut. The potential for drill skiving is magnified during a procedure that involves the drilling of sequential holes that are either overlapping or located close together, because the drill bit has a tendency to skive into previously drilled holes.

Traditional drill guides can be used to help control the location and alignment of a drill bit during a single hole drilling operation; however, they do not allow sufficient control of the location and orientation of several sequential drill holes that are either overlapping or located close together.

SUMMARY

The present disclosure relates, among other things, to surgical cutting systems and methods. In an embodiment, the surgical cutting system generally includes a drill guide, a drill guide sleeve, and a drill bit. The drill guide can be configured to be coupled to a trial implant, and includes a guide portion. Further, the drill guide can define a guide hole that extends through the guide portion along a guide hole axis. The drill guide sleeve can be configured to be at least partially received in the guide hole, and includes a sleeve body. Furthermore, the drill guide sleeve defines a first stop member and a sleeve opening disposed through the sleeve body. The drill bit can be configured to be at least partially received in the sleeve opening. Moreover, the drill bit defines a second stop member that is configured abut the first stop member so as to limit movement of the drill bit through the guide hole along the guide hole axis to a maximum cut depth. The guide hole can be oriented relative to the trial implant when the drill guide is coupled to the trial implant such that the guide hole is configured to guide the drill bit to advance through the guide hole along the guide hole axis into the vertebral body so as to create a drilled opening in the vertebral body. The drilled opening can be elongate along a drill axis that is substantially parallel to at least a portion of an upper surface or a lower surface of the trial implant.

According to an embodiment, the drill guide can further include a first spacer member and a second spacer member that is spaced from the first spacer member, the first and second spacer members elongate along a longitudinal direction, and the first and second spacer members spaced from each other along the transverse direction that is substantially perpendicular to the longitudinal direction, and the first and second spacer members are configured to engage corresponding first and second opposed surfaces of the trial implant.

In an embodiment, the guide hole axis is angularly offset with respect to the longitudinal direction, such that the drilled opening extends along a trajectory that is angularly offset with respect to the longitudinal direction. According to an embodiment, the drill guide can further include a drill guide body that extends from the guide portion along the longitudinal direction. The guide portion can protrude from the drill guide body along the transverse direction. The drill guide can define a drill guide opening that extends into the drill guide body. The drill guide opening can be configured to receive at least a portion of the trial implant such that insertion of the portion of the trial implant in the drill guide body opening causes the drill guide to be coupled to the trial implant. The drill guide opening can be elongate along the longitudinal direction.

In an embodiment, the surgical cutting system can further include a drill guide sleeve that is configured to be at least partially received in the guide hole. The drill guide sleeve can include a sleeve body. Further, the drill guide sleeve can define a sleeve opening disposed through the sleeve body. The sleeve opening can be configured to receive at least a portion of the drill bit. The drill guide sleeve can define the first stop member, and the second stop member is configured to contact the first stop member so as to define a cut depth that is substantially equal to an insertion depth of the chisel into the vertebral body.

According to an embodiment, the drill guide can include a plurality of first engagement members that at least partially define the guide hole. The drill guide sleeve can define a plurality of second engagement members that are configured to mate with the first engagement members so as to couple the drill guide sleeve to the drill guide. The first engagement members can be lobes that protrude from the guide portion into the guide hole. The second engagement members can be splines defined along at least a length sleeve of the sleeve body, the splines configured to mate with the lobes so as to couple the drill guide to the drill guide sleeve.

In accordance with an embodiment of the present disclosure, the guide hole can define a first portion and a second portion. The first portion defines a transverse dimension greater than the second portion. The drill guide sleeve can be sized to be inserted into the first portion, and is sized greater than the second portion. The drill guide sleeve can be at least one first drill guide sleeve sized to be inserted into the first portion, and the surgical cutting system further comprises at least one second drill guide sleeve sized to be inserted into the second portion. The first drill guide sleeve can define an internal diameter greater than that of the at least one second drill guide sleeve. The drill bit can be a first drill bit, and the surgical cutting system can further include a second drill bit having a smaller diameter than the first drill bit. The second drill bit can be sized to be guided through the at least one second drill guide sleeve. The second drill bit can define a stop member that is configured abut a complementary stop member supported by the guide portion so as to limit movement of the second drill bit through the guide hole along the guide hole axis, such that the second drill bit defines a maximum cut depth less than that of the first drill bit. The second drill bit can be configured to be guided along the second drill guide sleeve into a vertebral body, and the maximum cut depth of the second drill bit is greater than a thickness of a cortical wall of the vertebral body.

According to an embodiment, the drill guide can include a plurality of first engagement members that at least partially define the guide hole. The second drill guide sleeve can include a pair of drill guide sleeve. One of the pair of drill guide sleeves has a substantially smooth outer surface and the other of which defining a plurality of second engagement members configured to interlock with at least one of the plurality of first engagement members. The second drill guide sleeve can be configured to slide along the guide hole in the transverse direction without interlocking with the first engagement members. The second drill guide sleeve can have the substantially smooth outer surface defines an outer diameter sized less than a cross-sectional dimension of the guide hole as measured through at least one of the first engagement members. The surgical cutting system can further include a connection member connected between each of the pair of the at least one second drill guide sleeve. The first sleeve body can define a first cross-sectional dimension, and the second sleeve body defines a second cross-sectional dimension that is less than the first cross-sectional dimension.

The surgical cutting system can further include the trial implant that includes a support member and a trial spacer member that is connected to the supporting member. The trial spacer member can be sized to be inserted in an intervertebral space between adjacent vertebral bodies. The guide hole can be a first guide hole, and the guide member can define a second guide hole spaced from the first guide hole, such that the first guide hole is configured to be aligned with a first vertebral body. The second guide hole can be configured to be aligned with a second vertebral body, such that the trial implant is configured to be inserted into an intervertebral spaced defined between the first and second vertebra bodies.

The present disclosure also relates to a surgical cutting kit. In an embodiment, the surgical cutting kit includes a trial spacer member, a drill guide, a drill guide sleeve, and a drill bit. The trial spacer member can be sized to fit in an intervertebral space between first and second vertebral bodies, the trial spacer member defining an upper surface and a lower surface opposite the upper surface. The drill guide can be configured to be fixed with respect to the trial spacer member. The drill guide can include a guide portion. The drill guide can define a guide hole that extends through the guide portion along a guide hole axis. The drill guide sleeve can be configured to be at least partially received in the guide hole, and includes a sleeve body. Furthermore, the drill guide sleeve defines a sleeve opening disposed through the sleeve body. The drill bit can be configured to drill through the vertebral bodies. The drill bit can be configured to be at least partially received in the sleeve opening and guided through the guide hole along the guide hole axis so as to create a drilled opening in the first vertebral body. The guide hole can be oriented relative to the trial spacer member when the drill guide is fixed with respect to the trial spacer member such that the drilled opening is in substantial alignment with the upper cutting edge of the chisel when the chisel is guided along the trial spacer member and into the first vertebral body.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical instruments and methods of the present application, there is shown in the drawings preferred embodiments. It should be understood, however, that the application is not limited to the specific embodiments and methods disclosed, and reference is made to the claims for that purpose. In the drawings:

FIG. 1B is a posterior view of a vertebral body of the partial spinal column shown in FIG. 1A having an upper deep hole that extends into the cancellous bone of the vertebral body;

FIG. 1C is a medical elevation view of the vertebral body of FIG. 1B, showing the upper deep hole that extends into the cancellous bone;

FIG. 1D is a posterior view of the vertebral body of FIG. 1B having a plurality of shallow holes that extend at least into the cortical bone of the vertebral body;

FIG. 1E is a medial view of the vertebral body of FIG. 1D, showing the shallow holes that extend at least into the cortical bone of the vertebral body;

FIG. 1F is a posterior view of the vertebral body of FIG. 1B, showing the upper deep hole that extends into the cancellous bone and a plurality of overlapping shallow holes that extend into at least into the cortical bone;

FIG. 3B is a side cross-sectional view of the cutting guide of FIG. 3A, taken along section line 3B-3B;

FIG. 3C is a front elevation view of the cutting guide of FIG. 3A;

FIG. 4A is a perspective view of the guide member shown in FIG. 1A;

FIG. 4B is a side cross-sectional view of the guide member of FIG. 4A, taken along the section line 4A-4A;

FIG. 5A is perspective view of the second guide member of FIG. 1A;

FIG. 5B is a side cross-sectional view of the second guide member of FIG. 5A, taken along section line 5B-5B;

FIG. 6 is a perspective view of the first cutting tool shown in FIG. 1A;

FIG. 7 is a perspective view of the second cutting tool shown in FIG. 1A;

FIG. 8 is a side elevation view of the first cutting tool shown in FIG. 1A partially inserted in a first guide member sleeve of the first guide member shown in FIG. 1A;

FIG. 9 is a side elevation view of the second cutting tool shown in FIG. 1A partially inserted in a second guide sleeve of the second guide member shown in FIG. 1A;

FIG. 12A is a side elevation view of a partial spinal column and the trial disc implant shown in FIG. 1A at least partially disposed in an intervertebral space between adjacent vertebral bodies;

FIG. 12B is a side elevation view of the partial spinal column and the trial disc implant illustrated in FIG. 12A, and the cutting guide shown in FIG. 1A coupled to the trial disc implant;

FIG. 12C is a side elevation view of the partial spinal column, the trial disc implant, and the cutting guide shown in FIG. 12B, and the first guide member and the first cutting tool shown in FIG. 1A, wherein the trial disc implant and the cutting guide are in a first position relative to the intervertebral space;

FIG. 12D is a side elevation view of the partial spinal column, the trial disc implant, and the cutting guide shown in FIG. 12B, and the first guide member and the first cutting tool shown in FIG. 1A, wherein the trial disc implant and the cutting guide are in a second position relative to the intervertebral space;

FIG. 12E is a side elevation view of the partial spinal column, the trial disc implant, the cutting guide, the first guide member, and the first cutting tool illustrated in FIG. 12C, and the second guide member and the second cutting tool shown in FIG. 1A.

DETAILED DESCRIPTION OF ILLUSTRATIVE EMBODIMENTS

Figure 1A:
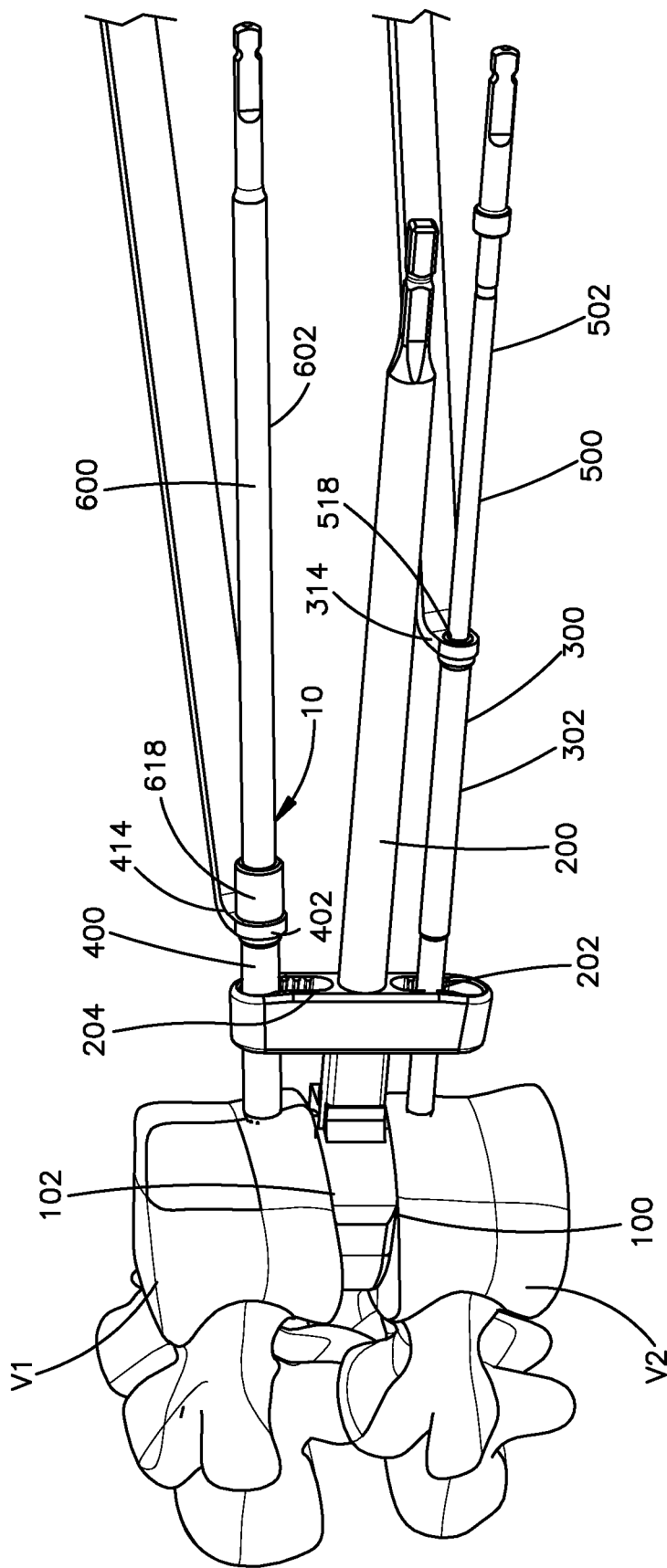
FIG. 1A is a perspective view of a surgical cutting system according to an embodiment of the present disclosure that includes a trial disc implant partially disposed in an intervertebral space between first and second vertebral bodies, a cutting guide, a first guide member, a first cutting tool, a second guide member, and a second cutting tool.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

With reference to FIGS. 1A-G, a surgical cutting system 10 is configured to prepare an intervertebral space for inserting a suitable intervertebral implant. The surgical cutting system 10 can be a surgical drilling system. In an embodiment, the surgical cutting system 10 can be used to prepare an intervertebral space for inserting an intervertebral implant 700 that includes at least one keel 702 that is configured to be inserted into a first vertebral body V1 or a second vertebral body V2 of a spinal column S. Examples of a suitable intervertebral implant is described and illustrated in U.S. Pat. No. 6,936,071 issued on Aug. 30, 2005, the entire disclosure of which is herein incorporated by reference. The surgical cutting system 10 can be part of a surgical disc replacement assembly that can be used for total disc replacement surgery. In a total disc replacement surgery, a diseased or degenerated intervertebral disc can be replaced with a suitable intervertebral implant, such as the intervertebral implant 700. Thus, the surgical disc replacement assembly can include the surgical cutting system 10 and one or more intervertebral implants 700.

With reference to FIG. 1A, in an embodiment, the surgical cutting system 10 can include a trial disc implant 100, a cutting guide 200, a first guide member 300, a second guide member 400, a first cutting tool 500, and a second cutting tool 600. The first cutting tool 500 can be a first drill bit 502. The second cutting tool 600 can be a second drill bit 602. The trial disc implant 100 can include a trial spacer member 102 that is sized to be disposed in an intervertebral space between the first vertebral body V1 and the second vertebral body V2. The cutting guide 200 can be configured to be coupled to the trial disc implant 100, and can define one or more guide holes. For example, in the depicted embodiment, the cutting guide 200 defines a first guide hole 202 and a second guide hole 204. Each guide hole 202, 204 can be configured to receive at least a portion of the first guide member 300 or at least a portion of the second guide member 400. The cutting guide 200 can be configured as a drill guide. Thus, the drill guide can be configured to be coupled to the trial implant 100. The first cutting tool 500 can be configured to be at least partially received in the first guide hole 202 or the second guide hole 204. Thus, the first drill bit 502 can be configured to be at least partially received in the first guide hole 202 or the second guide hole 204. The second cutting tool 600 can be configured to be at least partially received in the first guide hole 202 or the second guide hole 204. Thus, the first drill bit 602 can be configured to be at least partially received in the first guide hole 202 or the second guide hole 204.

Figure 1G:
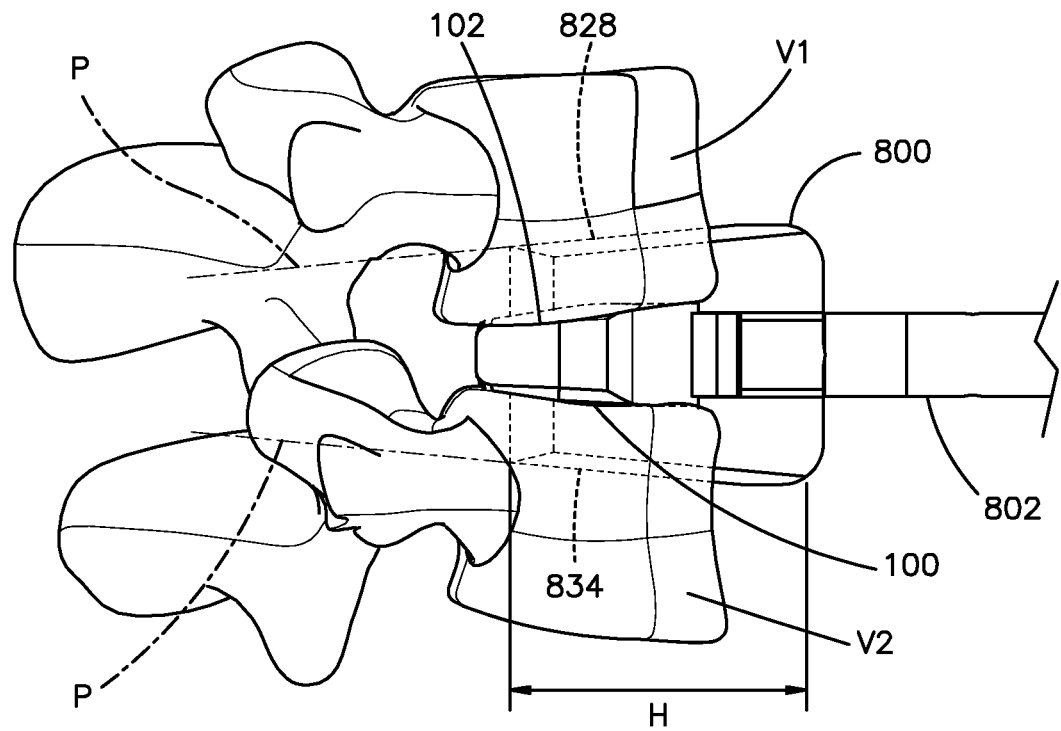
FIG. 1G is a medial view of a partial spinal column, showing the trial disc implant of FIG. 1A disposed between adjacent vertebral bodies and a chisel inserted into the spinal column.
Figure 1H:
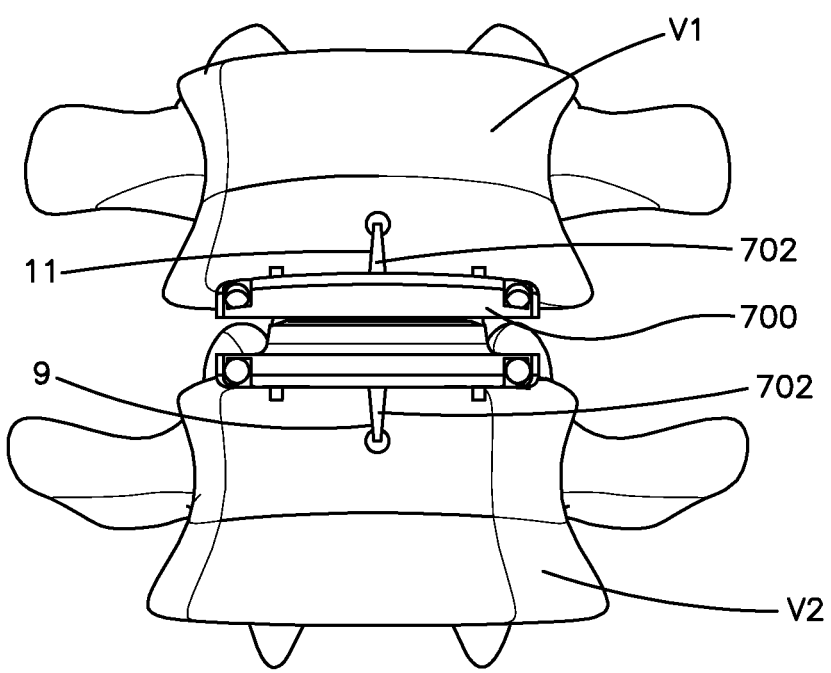
FIG. 1H is a posterior view of an intervertebral implant disposed in an intervertebral space between adjacent vertebral bodies.

With continuing reference to FIG. 1A, in operation, the trial disc implant 100 can be placed in the intervertebral space between the first vertebral body V1 and the second vertebral body V2 to determine the appropriate implant footprint, lordotic angle, and disc height of the intervertebral implant 700 (FIG. 1H). Accordingly, the surgical cutting system 10 can include a plurality of trial disc implants 100 with spacer members 102 of different shapes and sizes. The cutting guide 200 can be coupled to the trial disc implant 100 that is at least partially disposed in the intervertebral space such that the first and second guide holes 202 and 204 are aligned with at least one of the first vertebral body V1 or the second vertebral body V2. In the depicted embodiment, the cutting guide 200 can be coupled to the trial implant 100 such that the first guide hole 202 is aligned to the first vertebral body V1 and the second guide hole 204 is aligned with the second vertebral body V2. At least a portion of the first guide member 300 can be disposed through the first guide hole 202. Once the first guide member 300 is disposed through the first guide hole 202, the first cutting tool 500 can be advanced through the first guide member 300 and into the first vertebral body V1 to fix the position of the cutting guide 200 relative to the spinal column S. At least a portion of the second guide member 400 can be inserted through the second guide hole 204. The second cutting tool 500 can then be advanced through the second guide member 400 and into second vertebral body V2 to create a first opening 1 (FIGS. 1B-C) that extends into through the cortical bone and into the cancellous bone of the first vertebral body V1. In an embodiment, the second cutting tool 500 can have a substantially rounded, such as circular, semi-circular, or oval, cross-sectional shape such that it can create a first opening 1 that defines a substantially rounded cross-sectional shape. The second guide hole 204 can be oriented relative such that the second cutting tool 600 moves along a trajectory that matches the trajectory that will following a third cutting tool 800, such as a chisel 802 (FIG. 1G). As discussed below in detail, the third cutting tool 800 (FIG. 1G) can be advanced along the trial disc implant 100 and into the first vertebral body V1 and the second vertebral body V2 to create one more apertures that are configured to receive one or more keels 702 of the intervertebral implant 700.

With continuing reference to FIG. 1A, the cutting guide 200 (e.g., the drill guide) can be configured to support a first stop member 314 (or 316 as seen in FIG. 4A) as discussed in detail below. The cutting tool 500, such as the drill bit 502, can define a complementary second stop member 518 that is configured to abut the first stop member 314 (or 316) so as to limit movement of the cutting tool 500 (e.g., drill bit 502) through the guide hole 202 (or 204) to a maximum cut depth. The cutting guide 200 (e.g., the drill guide) can be configured to support a first stop member 414 (or 416 as seen in FIG. 5A) as discussed in detail below. The cutting tool 600, such as the drill bit 602, can define a complementary second stop member 618 that is configured to abut the first stop member 414 (or 416) so as to limit movement of the cutting tool 600 (e.g., drill bit 602) through the guide hole 202 (or 204) to a maximum cut depth.

With reference to FIGS. 1B-C, the first opening 1 can be elongate along a first cutting axis 2 that is substantially aligned with the trajectory that follows an edge of the third cutting tool 800 (FIG. 1G) when the third cutting tool is advanced along the trial disc implant 100 and into the second vertebral body V2. Specifically, the first opening 1 defines a first closed end 3 that is disposed in the cancellous bone of the second vertebral body V2, and a second open end 4 that is located at the cortical bone of the second vertebral body V2. The first closed end 3 is spaced from the second open end 4 in a direction along the cutting axis 2. The cutting axis 2 can also be a drill axis. The second open end 4 leads to the exterior of the second vertebral body V2. The first opening 1 can have a substantially rounded, such as circular or oval, cross-sectional shape to prevent, or at least inhibit, the formation of stress risers in the second vertebral body V2, thereby precluding, or at least hindering, the creation of stress cracks in the second vertebral body V2. It is envisioned that an opening can also be created in the first vertebral body V1 that is substantially aligned with the trajectory that follows another edge of the third cutting tool 800 (FIG. 1G).

With reference to FIGS. 1D-E, the second cutting tool 600 can also be used to remove portions of the cortical bone of the second vertebral body V2 to facilitate advancement of the third cutting tool 800 (FIG. 1G) into the vertebral body V2 as discussed in detail below. Before or after creating the first opening 1, the second cutting tool 600 can be moved along the second guide hole 204 to create one or more second openings 5 that extend at least into the cortical bone of the second vertebral body V2. Each of the second openings 5 can define a second cutting axis, such as the second cutting axis 6. Each of the second cutting axes 6 can be oriented at an oblique angle relative to the first cutting axis 2. The second cutting axes 6 can be substantially parallel to each other. In the depicted embodiment, the second openings 5 are substantially aligned along the cranial direction C1 and the caudal direction C2 of the second vertebral body V2. Furthermore, the second openings 5 can define cutting axes that are substantially parallel to one another. Each of the second openings 5 can define a first closed end 7 that can be disposed in the cortical wall of the second vertebral body V2, and a second open end 8 that leads to the exterior of the second vertebral body V2. The first closed end 7 can be spaced from the second open end 8 along the second cutting axis 6. It is envisioned that the second openings 5 can also be created in the first vertebral body V1 using the cutting tools described in the present disclosure. The openings 5 can overlap with one another as shown in FIG. 1F. Regardless of the exact position of the openings 5, the openings 5 are created to remove additional cortical wall after making the opening 1 to thereby facilitate insertion of a cutting tool through the vertebral bodies. As seen in FIGS. 1D and 1F, the openings 5 can extend all the way to the endplate of the vertebral body V2. However, it is envisioned that the openings 5 do not necessarily extend to the endplate of the vertebral body V2.

With reference to FIG. 1G, the cutting guide 200, the first cutting guide 200, the first guide member 300, the second guide member 400, the first cutting tool 500, and the second cutting tool 600 can be removed from the patient, while leaving the trial spacer member 102 of the trial disc implant 100 disposed in the intervertebral space between the first vertebral body V1 and the second vertebral body V2. The third cutting tool 800 can be a chisel 802, and is configured to cut bone, such as the first vertebral body V1 and the second vertebral body V2. The third cutting tool 800, such as a chisel 802, can then be advanced along the trial disc implant 100 and toward the first vertebral body V1 and the second vertebral body V2. Specifically, third cutting tool 800 can be advanced into the first vertebral body V1 and the second vertebral body V2 to create a first aperture 9 (FIG. 1H) in the first vertebral body V1 and a second aperture 11 (FIG. 1H) in the second vertebral body V2. The third cutting tool 800 can be configured to be advanced along the trial implant 100 and toward the vertebral bodies to a maximum insertion depth H (also referred to as insertion depth). Also, the third cutting tool 800 can include outer cutting edges 828 and 834 that are configured to be travel along a corresponding trajectory P when the cutting tool 800 is advanced along the trial implant 100 and inserted into the vertebral bodies V1 and V2. Each of the first aperture 9 and the second aperture 11 is configured to receive at least one keel 702 of the intervertebral implant 700 (FIG. 1H).

With reference to FIG. 1H, after creating the first aperture 9 and the second aperture 11, the intervertebral implant 700 can be inserted in the intervertebral space defined between the first vertebral body V1 and the second vertebral body V2. During insertion, the keels 702 can be positioned in the first aperture 9 and the second aperture 11. In the depicted embodiment, the intervertebral implant 700 includes two keels 702. It is envisioned, however, that the intervertebral implant 700 can have more or fewer keels 702. Accordingly, more or fewer apertures can be made in at least one of the first vertebral body V1 or the second vertebral body V2 to accommodate the corresponding number of keels 702.

Figure 2:
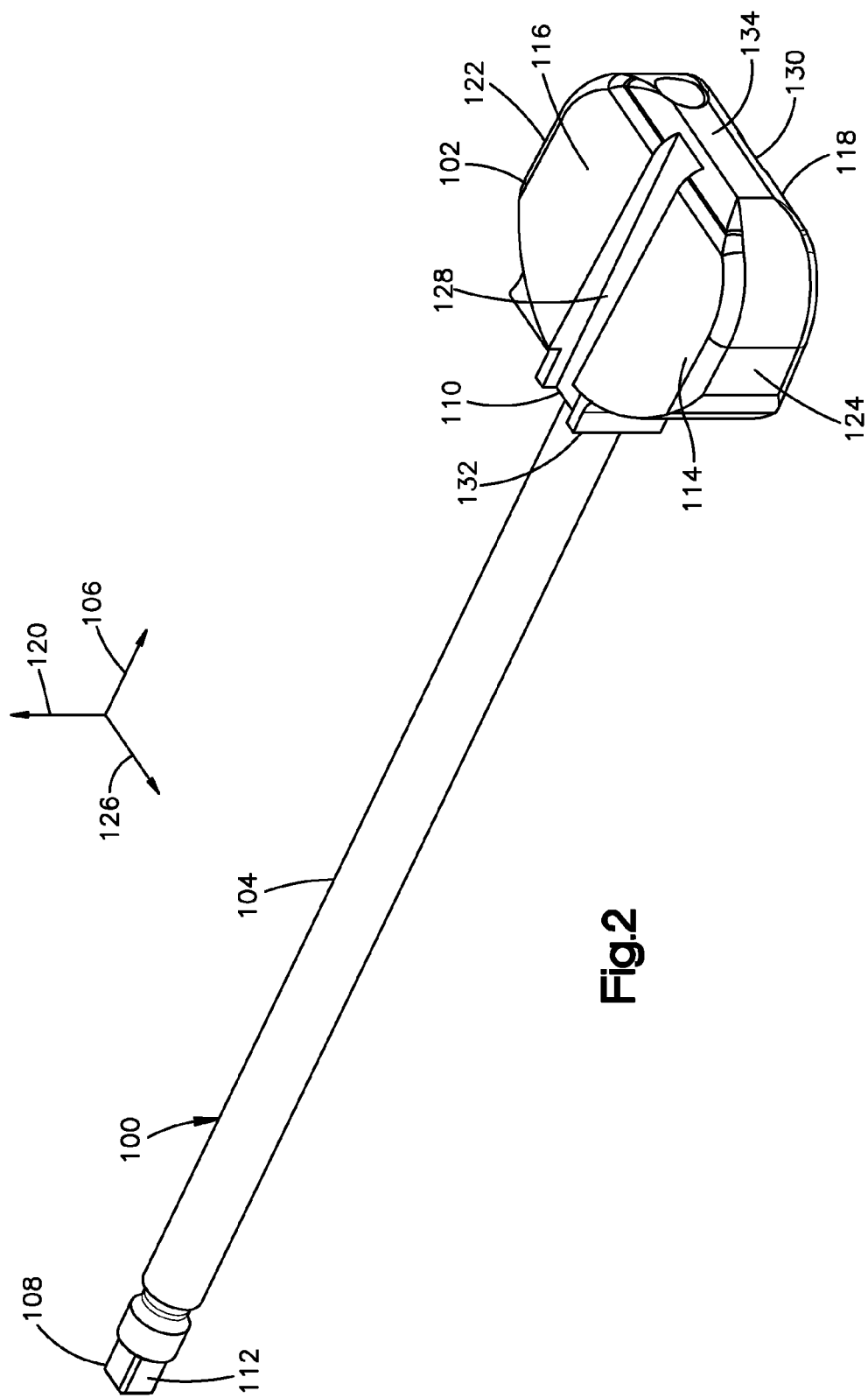
FIG. 2 is a perspective view of the trial disc implant shown in FIG. 1A.

With reference to FIG. 2, the trial disc implant 100 can include the trial spacer member 102 and a trial support member 104, such as a rod, that is connected to the trial spacer member 102. As discussed above, the trial spacer member 102 can be shaped and sized to fit in the intervertebral space between the first vertebral body V1 (FIG. 1A) and the second vertebral body V2 (FIG. 1A). The trial support member 104 can be directly or indirectly connected to the trial spacer member 102. It is envisioned that the trial support member 104 can be monolithically formed with the trial spacer member 102. The trial spacer member 102 can be sized to be inserted in an intervertebral space between first and second vertebral bodies V1 and V2. The trial support member 104 can be elongate along a longitudinal direction 106 so as to define a first end 108 and a second end 110. The first end 108 can be spaced from the second end 110 along the longitudinal direction 106. The second end 110 can be connected to the trial spacer member 102. The supporting member 106 can further include an attachment member 112 at the first end 108. The attachment member 112 can be configured to be attached to a handle to allow manipulation of the trial disc implant 100 through the handle. In the depicted embodiment, attachment member 112 can be constructed as male member, such as polygonal key, that is configured to be securely received in a corresponding female member in the handle such as a polygonal socket. It is contemplated, however, the attachment member 112 can be any other suitable device capable of coupling the trial support member 104 to a handle.

With continuing reference to FIG. 2, the trial spacer member 102 can be attached to the second end 110 of the trial support member 104 and can include a spacer body 114. The spacer body 114 can be shaped and sized to fit in the intervertebral space between the first vertebral space V1 and the second vertebral space V2. The spacer body 114 defines an upper surface 116 and a lower surface 118 opposite to the upper surface 116. The upper surface 116 can be spaced from the lower surface 118 along a transverse direction 120 that is substantially perpendicular to the longitudinal direction 106. The spacer body 114 can also define a first side surface 122 and a second side surface 124 opposite from the first side surface 122. The first side surface 122 can be spaced from the second side surface 124 along a lateral direction 126 that is substantially perpendicular to the transverse direction 120. The spacer body 114 further defines a first spacer end 132 and a second spacer end 134 opposite to the first spacer end 132. The second spacer end 132 is spaced from the first spacer end 132 along the longitudinal direction 106. The spacer member 104 can define a first groove 128 that extends into the upper surface 116, and a second groove 130 that extends into the lower surface 118. Each of the first groove 128 and the second groove 130 can be elongate along the longitudinal direction 106. That is, each of the first groove 128 and the second groove 130 can be elongate along a direction from the first spacer end 132 toward the second spacer end 134. The first groove 128 and the second groove 130 are each configured and sized to receive a portion of the third cutting tool 800 (FIG. 1G) to guide the advancement of the third cutting tool 800 toward the first vertebral body V1 (FIG. 1A) and the second vertebral body V2 (FIG. 1A) when the trial spacer member 102 is disposed in the intervertebral space. As discussed above, the trial disc implant 100 can be placed in the intervertebral space between the first vertebral body V1 and the second vertebral body V2 to determine the appropriate implant footprint, lordotic angle, and disc height of the intervertebral implant 700 (FIG. 1H). Consequently, the surgical cutting system 10 can include a plurality of trial disc implants 100 with spacer members 102 of different shapes and sizes. It is envisioned that the surgical cutting system 10 can include any other suitable trial disc implant.

Examples of suitable trial disc implants are described and illustrated in U.S. Pat. No. 7,491,204 issued on Feb. 17, 2009, the entire disclosure of which is herein incorporated by reference. The surgical cutting system 10 can be part of a surgical cutting kit that includes one or more cutting tools, such as a chisel 800 described in detail below. In an embodiment, the surgical cutting kit can include a trial spacer member 102, a cutting tool, such as a chisel, a cutting guide 200, such as a drill guide, and a drill bit as described below. The surgical cutting kit can include, among other things, any of the devices, apparatus, or assemblies described herein in any conceivable combination.

Figure 3A:
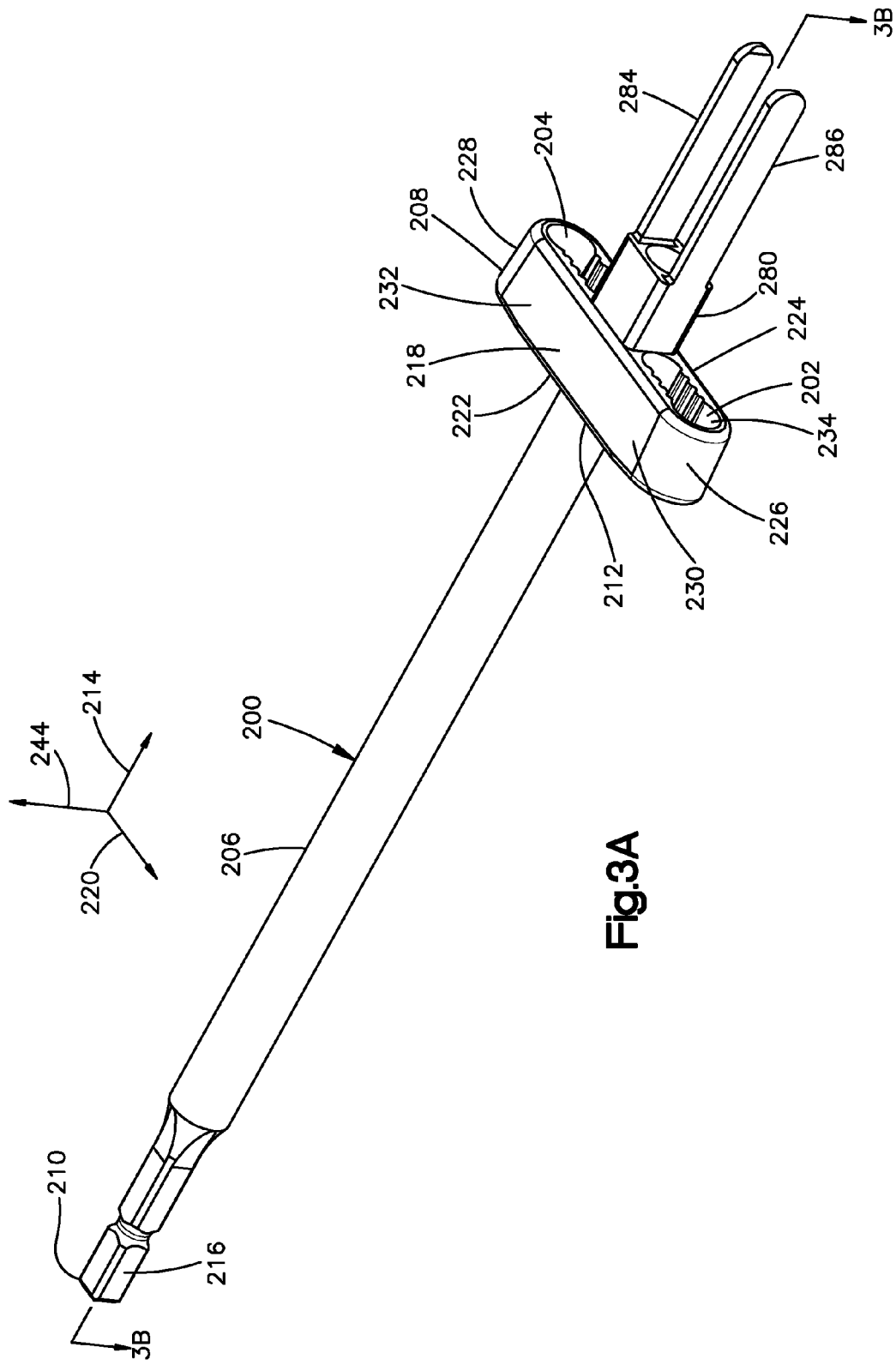
FIG. 3A is a perspective view of the cutting guide shown in FIG. 1A.

With reference to FIG. 3A, the cutting guide 200 is configured to guide the movement at least one of the first cutting tool 500 or the second cutting tool 600 toward at least one of the first vertebral body V1 or the second vertebral body V2 when the cutting guide 200 is coupled to the trial implant 100 and the trial spacer member 102 is disposed in the intervertebral space between the first vertebral body V1 and the second vertebral body V2. The cutting guide 200 can include a cutting guide body 206 and a guide portion 208 connected to the cutting guide body 206. The cutting guide body 206 is configured to support guide portion 208. The cutting guide 200 can be constructed as a drill guide. Thus, the cutting guide body 206 can be a drill guide body. The drill guide body can extend from the guide portion 208 along the longitudinal direction 214. The guide portion 208 can be a drill guide portion. Moreover, the guide portion 208 can protrude from the cutting guide body 206 (e.g., drill guide body) along the transverse direction 220.

With continuing reference to FIG. 3A, the cutting guide body 206 can define a first end 210 and a second end 212 that is spaced from the first end 210 along a longitudinal direction 214. Thus, the cutting guide body 206 can be elongate along the longitudinal direction. The cutting guide body 206 can include an attachment member 216 that is configured to be attached to a handle to allow manipulation of the cutting guide 200 through the handle. The attachment member 216 can be located at or near the first end 210 of the cutting guide body 206. In the depicted embodiment, the attachment member 216 can be constructed as a male member, such as a polygonal key, that is configured to be securely received in a corresponding female member in the handle such as a polygonal socket. It is envisioned, however, that the attachment member 216 can be any other suitable device capable of coupling the cutting guide 200 to a handle. The second end 212 of the cutting guide body 206 can be directly or indirectly connected to the guide portion 208.

With continuing reference to FIG. 3A, the guide portion 208 can be mounted to the cutting guide body 206, and can include guide portion body 218 that is elongate along a transverse direction 220. The transverse direction 220 can be substantially perpendicular to the longitudinal direction 214. The guide portion body 218 can define a first transverse end 226 and a second transverse end 228 opposite to the first transverse end 226. The first transverse end 226 is spaced from the second transverse end 228 along the transverse direction 220. The guide portion body 218 can further define a first longitudinal end 222 and a second longitudinal end 224 opposite to the first longitudinal end 22. The first longitudinal end 222 is spaced from the first longitudinal end 222 along the longitudinal direction 214. The guide portion body 218 can include a first guide prong 230 and a second guide prong 232. The first guide prong 230 can be closer to the first transverse end 226 than the second transverse end 228. The second guide prong 232 can be closer to the second transverse end 228 than the first transverse end 226. The first guide prong 230 can define the first guide hole 202, and the second guide prong 232 defines the second guide hole 204. Moreover, each of the guide holes 202 and 204 can be elongate along the transverse direction 220. The first guide hole 202 can extend along through the guide portion 208 along a first guide hole axis 203 (FIG. 3B), and the second guide hole 204 can extend through the guide portion 208 along a second guide hole axis 205. The first guide hole axis 203 (FIG. 3B) can be angularly offset with respect to the longitudinal direction 214, such that the drilled opening 1 extends along a trajectory, which can be defined by the cutting axis 2, that is angularly offset with respect to the longitudinal direction 214. The second guide hole axis 205 (FIG. 3B) can be angularly offset with respect to the longitudinal direction 214, such that the drilled opening 1 extends along a trajectory, which can be defined by the cutting axis 2, that is angularly offset with respect to the longitudinal direction 214. As discussed above, the cutting axis 2 can be a drill axis. The drilled opening 1 can be elongate along a drill axis 2 that is substantially parallel to at least a portion of an upper surface 116 or a lower surface 118 of the trial implant 100.

With continuing reference to FIG. 3A, the cutting guide 200 can further include abutting member 280 that is configured to abut the at least a portion of the trial spacer member 102 when the cutting guide 200 is coupled to the trial disc implant 100 in order to enhance stability of the connection between the cutting guide 200 and the trial disc implant 100. The abutting member 280 can be connected to the guide portion 208. In the depicted embodiment, the abutting member 280 can be directly or indirectly connected to the second longitudinal end 224 of the guide portion 208.

With continuing reference to FIG. 3B, the cutting guide 200 can further include at least one spacer member 284, 286, such a protrusions, that are configured to engage at least one of the upper surface 116 or the lower surface 118 of the trial spacer member 102 when the cutting guide 200 is coupled to the trial disc implant 100 in order to firmly secure the cutting guide 200 to the trial disc implant 100. For example, the first spacer member 284 can be configured to engage the upper surface 116, and the second spacer member 286 can be configured to engage the lower surface 118 (FIG. 2). In the depicted embodiment, the cutting guide 200 can include a first spacer member 284 and a second spacer member 286 that is spaced from the first spacer member 284 along the transverse direction. The first spacer member 284 and the second spacer member 286 can protrude from the abutment member 280 along the longitudinal direction 214. In particular, the first spacer member 284 and the second spacer member 286 can be oriented substantially parallel to each other. Moreover, at least one of the first spacer member 284 or the second spacer member 286 can be substantially planar, such as substantially flat. The first and second spacer members 284 and 286 can be configured and sized to be received in corresponding grooves 128 and 130. The first spacer member 284 and the second spacer member 286 can be elongate along the longitudinal direction 214. The first and second spacer members 284 and 286 can be spaced from each other along the transverse direction 220 that is substantially perpendicular to the longitudinal direction 214.

With continuing reference to FIG. 3B, the cutting guide 200 can further define an cutting guide opening 282 that extends along the cutting guide body 206, the guide portion 208, and the abutment member 280. The cutting guide opening 282 can be a drill guide opening. The cutting guide opening 282 can extend in a direction from second end 212 toward the first end 210. That is, the cutting guide opening 282 can be disposed along the cutting guide 200 in the longitudinal direction 214. The cutting guide opening (e.g., the drill guide opening) can extend into the cutting guide body 206 (e.g., drill guide body). In particular, the cutting guide opening 282 can be configured and sized to receive at least a portion of the trial support member 104 (FIG. 2). In other words, the cutting guide opening 282, such as the drill guide opening, can be configured and sized to receive a portion of the trial implant 100 such that insertion of the trial implant 100 in the cutting guide opening 282 causes the cutting guide 200 (e.g., drill guide) to be coupled to the trial implant 100. Consequently, the cutting guide body 206 can be slid over at least a portion of the trial support member 104 in order to couple the cutting guide 200 to the trial dis implant 100 (FIG. 2). Thus, the cutting guide opening 282 can have a shape and size suitable to receive at least a portion of the trial support member 104. For example, the cutting guide opening 282 can have a substantially cylindrical shape. In the depicted embodiment, the cutting guide opening 282 can include a closed end 288 and an open end 290 that is spaced from the closed end 288 along the longitudinal direction 214. The open end 290 can be located at the abutting member 280 and leads to the outside of the cutting guide 200. The closed end 288 can be located along the cutting guide body 206. The cutting guide opening 282 can be configured as a drill guide opening. The cutting guide opening 282 can be elongate along the longitudinal direction 214.

With reference to FIG. 3C, the first guide prong 230 defines a first inner surface 234 that in turn defines the first guide hole 202. The first guide hole 202 extends through the first longitudinal end 222 (FIG. 3A) and the second longitudinal end 224 (FIG. 3A) of the cutting guide portion body 218, and can be elongate along the transverse direction 220. Furthermore, the first guide hole 202 defines a first closed end 236 and a second closed end 238 opposite to the first closed end 236. The first closed end 236 can be spaced from the second closed end along the transverse direction 220. The first guide hole 202 can further define a first lateral end 240 and a second lateral end 242 opposite to the first lateral end 240. The first lateral end 240 can be spaced from the second lateral end 242 along a lateral direction 244.

With continuing reference to FIG. 3C, the first guide hole 202 can include a first end portion 246, a second end portion 250, and a middle portion 248 that is located between the first end portion 246 and the second end portion 250. The first end portion 246 can be closer to the first closed end 236 than the second end portion 250. The first end portion 246 defines a first cross-sectional dimension 252 that is defined from the first lateral end 240 to the second lateral end 242. The middle portion 248 defines a second cross-sectional dimension 254 that is defined from the first lateral end 240 to the second lateral end 242. The first cross-sectional end 252 can be larger than the second cross-sectional end 254 in order to facilitate insertion of the guide member 300 or the guide member 400 through the first end portion 246. The second end portion 250 can define a cross-sectional dimension that is defined from the first lateral end 240 to the second lateral end 242. The cross-sectional dimension of the second end portion 250 can be substantially similar or identical to the second cross-sectional dimension 254.

The first end portion 246 can be referred to as a first portion, and the middle portion 248 can be referred to as a second portion. The first guide hole 202 can thus define the first portion 246 and the second portion 250. The first portion 246 can define the cross-sectional dimension 252. The cross-sectional dimension 252 can also be referred to as a first transverse dimension 252. The second portion 250 can define the cross-sectional dimension 254. The cross-sectional dimension 254 can also be referred to as a second transverse dimension 254. The first transverse dimension 252 can be greater than the transverse dimension 254. The drill With continuing reference to FIG. 3C, the first guide prong 230 can include a mating feature 255 that is configured to mate with a portion of the guide member 300 (FIG. 1A) so as to fix the position of the guide member 300 relative to the cutting guide 200. In an embodiment, the mating feature 255 can include one or more engagement members 256, such as protrusions or lobes, that protrude from the inner surface 234 in a direction toward the first guide hole 202. Specifically, the engagement members 256 are disposed along the first lateral end 240 the second lateral end 242 of the first guide hole 202. In the depicted embodiment, the engagement members 256 can only be disposed along the middle portion 248 of first guide hole 202, and are not necessarily located along the first end portion 246 and the second end portion 250 of the first guide hole 202. As discussed in detail below, the engagement members 256 are configured to mate with a portion of the first guide member 300 so as to lock the position of the first guide member 300 relative to the cutting guide 200.

With continuing reference to FIG. 3C, the second guide prong 232 can be substantially similar to the first guide prong 230. In an embodiment, the second guide prong 232 defines a second inner surface 258 that in turn defines the second guide hole 204. The second guide hole 204 extends through the first longitudinal end 222 (FIG. 3A) and the second longitudinal end 224 (FIG. 3A) of the cutting guide portion body 218, and can be elongate along the transverse direction 220. Furthermore, the second guide hole 204 defines a first closed end 260 and a second closed end 262 opposite to the first closed end 260. The first closed end 260 can be spaced from the second closed end 262 along the transverse direction 220. The second guide hole 204 can further define a first lateral end 264 and a second lateral end 266 opposite to the first lateral end 264. The first lateral end 264 can be spaced from the second lateral end 266 along the lateral direction 244.

With continuing reference to FIG. 3C, the second guide hole 204 can include a first end portion 268, a second end portion 272, and a middle portion 270 that is located between the first end portion 268 and the second end portion 272. The first end portion 268 can be closer to the first closed end 260 than the second end portion 262. The first end portion 268 defines a first cross-sectional dimension 274 that is defined from the first lateral end 264 to the second lateral end 266. The middle portion 270 defines a second cross-sectional dimension 276 that is defined from the first lateral end 264 to the second lateral end 266. The first cross-sectional dimension 274 can be larger than the second cross-sectional dimension 276 in order to facilitate insertion of the guide member 300 or the guide member 400 through the first end portion 268. The second end portion 272 can define a cross-sectional dimension that is defined from the first lateral end 264 to the second lateral end 266. The cross-sectional dimension of the second end portion 272 can be substantially similar or identical to the second cross-sectional dimension 276. The first end portion 268 can be referred to as a first portion 268, and the middle portion 270 can be referred to as the second portion 270. Thus, the second guide hole 204 can define the first portion 268 and the second portion 270. The first portion 268 can define the first cross-sectional dimension 274, which can be referred to as the first transverse dimension. The second portion 270 can define the second cross-sectional dimension, which can be referred to as the second transverse direction. The first transverse direction 274 can be greater than the second transverse direction 276.

With continuing reference to FIG. 3C, the second guide prong 232 can include a mating feature 277 that is configured to mate with a portion of the guide member 300 (FIG. 1A) so as to fix the position of the guide member 300 relative to the cutting guide 200. The mating feature 277 can include one or more engagement members 278, such as protrusions or lobes, that protrude from the second inner surface 258 in a direction toward the second guide hole 204. Specifically, the engagement members 256 can be disposed along the first lateral end 264 and the second lateral end 266 of the second guide hole 204. In the depicted embodiment, the engagement members 278 can only be disposed along the middle portion 270 of second guide hole 204, and are not necessarily located along the first end portion 268 and the second end portion 272 of the second guide hole 204. As discussed in detail below, the engagement members 278 can be configured to mate with a portion of the first guide member 300 so as to lock the position of the first guide member 300 relative to the cutting guide 200. As discussed above, the cutting guide 200 can be a drill guide. Thus, the drill guide can include a plurality of first engagement members 256 and 278. The first engagement members 256 can at least partially define the first guide hole 202. The first engagement members 278 can at least partially define the second guide hole 204.

With reference to FIG. 4A, the first guide member 300 can guide the movement of a cutting tool, such as a drill bit, toward the first vertebral body V1 or the second vertebral body V2 (FIG. 1A). The first guide member 300 can also server to protect soft tissue while advancing a cutting tool, such as a drill bit, toward the first vertebral body V1 or the second vertebral body V2. In the depicted embodiment, the first guide member 300 can include a first guide sleeve 304, a second guide sleeve 306, and a first guide member body 302 connected between the first guide sleeve 304 and the second guide sleeve 306. The first guide member 300 can be constructed as a first drill guide. Thus, the first guide member body 302 can be a drill guide body. The first guide sleeve 304 and the second guide sleeve 306 can each be configured as drill guide sleeves. The first guide member body 302 can be configured as a connection member, such as a bar.

With continuing reference to FIG. 4A, the first guide member body 302 can be configured as a connecting member capable of interconnecting the first guide sleeve 304 and the second guide sleeve 306. In the depicted embodiment, the first guide member body 302 can be constructed as a bar, and can be elongate along a longitudinal direction 310. The first guide member body 302 can include a first end 312 and a second end 313 that is spaced from the first end 312 along the longitudinal direction 310. Furthermore, the first guide member body 302 can have a substantially planar configuration. It is envisioned, however, that the first guide member 302 can alternatively have other suitable configurations.

With continuing reference to FIG. 4A, the first guide member 300 can define a first stop member 314, such as a flange, that protrudes from the first end 312 of the first guide member body 302 and another first stop member 316, such as a flange, that protrudes from the second end 313. The first stop member 314 can be configured to attach the first guide sleeve 304 to the first guide member body 302. The other first stop member 316 can be configured to attach the second guide sleeve 306 to the first guide member body 302. The first stop member 314 and the other first stop member 316 each can protrude from the first guide member body 302 at an oblique angle relative to the longitudinal direction 310.

With continuing reference to FIG. 4A, the first guide sleeve 304 can include a first guide sleeve body 328. The first guide sleeve body 328 can have a substantially cylindrical shape, and can define a first end 324 and a second end 326 opposite to the first end 324. The first end 324 can be spaced from the second end 326 along a first angled direction 330 that is oriented at an oblique angle relative to the longitudinal direction 310. The first guide sleeve body 328 can define an outer surface 318 that extends from the first end 324 to the second end 326. The outer surface 318 can include a substantially smooth portion 320 and an attachment portion 322. The attachment portion 322 of the outer surface 318 is not necessarily smooth. The smooth portion 320 can be located closer to the first end 324 than to the second end 326. The attachment portion 322 can be located closer to the second end 326 than to the first end 324, and can include a mating feature 332 that is configured to mate with either the mating feature 255 or the mating feature 277 of the cutting guide 200 so that the guide member 300 can be fixed to the cutting guide 200. In the depicted embodiment, the mating feature 332 can include engagement members 336, such as splines, ridges, teeth, or a combination thereof, disposed along the attachment portion 322 of the outer surface 318. For example, the engagement members 336 can be elongate along the first angled direction 330. Regardless of the specific shape or orientation, the engagement members 336 can be configured to mate with either the engagement members 256 or engagement members 278 in order to lock the guide member 300 to the cutting guide 200. As discussed above, the first guide sleeve 304 can be configured as a drill guide sleeve. Thus, the drill guide sleeve can define a plurality of second engagement members 336 that are configured to mate with the first engagement members 256 and 278 so as to couple the drill guide sleeve 304 to the drill guide 200. The drill sleeve 304 can be configured to define the second engagement members 336 to interlock with at least one of the first engagement members 256 or 278.

In addition to the engagement members 336, the first guide sleeve 304 can further include a plurality of teeth 338 that protrude from the first guide sleeve body 328 in a direction away from the first end 324. The teeth 338 can specifically protrude from the second end 326 of the first guide sleeve body 328, and can be configured to engage, such as penetrate, the first vertebral body V1 or the second vertebral body V2, to fix the position of the first guide sleeve 304 relative to either the first vertebral body V1 or the second vertebral body V2.

With continuing reference to FIG. 4A, the second guide sleeve 306 can include a second guide sleeve body 340. The second guide sleeve body 340 can have a substantially cylindrical shape, and can define a first end 342 and a second end 344 opposite to the first end 342. The first end 342 can be spaced from the second end 344 along a second angled direction 346 that is oriented at an oblique angle relative to the longitudinal direction 310. The second guide sleeve body 340 can define an outer surface 348 that extends from the first end 342 to the second end 344. The outer surface 348 can be entirely smooth. Thus, the guide sleeve 306 can have a substantially smooth outer surface 348. The drill guide sleeve 304 that has the substantially smooth outer surface 348 can define an outer cross-sectional dimension, such as a diameter, that is less than the cross-sectional dimension 254 of the first guide hole 202 or the cross-sectional dimension of the second guide hole 204. The second guide sleeve body 340 can include a first portion 350, a second portion 352, and a shoulder 354 disposed between the first portion 350 and the second portion 352. The shoulder 354 can separate the first portion 350 from the second portion 352. The first portion 350 can be spaced from the second portion 352 along the second angled direction 346. In the depicted embodiment, the first portion 350 can be located closer to the first end 352 than the second end 344. The second portion 352 can be located closer to the second end 344 than the first end 342. The shoulder 352 changes the cross-sectional dimension of the second guide sleeve body 306 such that the cross-sectional dimension of the first portion 350 is larger than the cross-sectional dimension of the second portion 352. The second guide sleeve 306 can further include one or more teeth 356 that protrude from second guide sleeve body 340 in a direction away from the first end 342 along the second angled direction 346. The teeth 356 can specifically protrude from the second end 344 of the second guide sleeve body 340, and can be configured to engage, such as penetrate, the first vertebral body V1 or the second vertebral body V2 to fix the position of the second guide sleeve 306 relative to either the first vertebral body V1 or the second vertebral body V2.

The first and second guide sleeves 304 and 306 can be configured as drill sleeves. Thus, the first guide member 300 can include drill sleeves 304 and 306. Each of the drill sleeves 304 and 306 can be sized to be at least partially inserted in the second portion 248 and the second portion 270 (FIG. 3C). The drill sleeve 306 can be configured to slide along the guide hole 202 or 204 in the transverse direction 220 without interlocking with the first engagement members 256 or 278.

With reference to FIG. 4B, the first guide sleeve body 328 can further define an inner surface 319 opposite to the outer surface 318. The inner surface 319 can define a first guide sleeve opening 321 that is elongate along the first angled direction 330. The first guide sleeve opening 321 can extend along a direction from the first end 324 toward the second end 326. In the depicted embodiment, the first guide sleeve opening 321 extends from the first end 324 to the second end 326, and can define a first open end 323 and a second open end 325 in order to allow at least a portion of the first cutting tool 500 (FIG. 1A) to be inserted through the first guide sleeve body 328. The first open end 323 can be spaced from the second open end 325 along the first angled direction 330. Thus, the first and the second guide sleeves 304 and 306 can be configured as drill guide sleeves. Thus, the drill guide sleeves 304 and 306 can each be configured and sized to receive at least partially received in the guide hole 202 (or 204). The sleeve opening 321 can be configured and sized to receive at least a portion of the cutting tool 500, such as the drill bit 502.

With continuing reference to FIG. 4B, the second guide sleeve body 340 can further define an inner surface 349 opposite to the outer surface 348. The inner surface 349 can define a second guide sleeve opening 351 that is elongate along the second angled direction 346. The second guide sleeve opening 351 can extend along a direction from the first end 342 toward the second end 344. In the depicted embodiment, the second guide sleeve opening 351 extends from the first end 342 to the second end 344, and can define a first open end 353 and a second open end 355 in order to allow at least a portion of the first cutting tool 500 (FIG. 1A) or the second cutting tool 600 (FIG. 1A) to be inserted through the second guide sleeve body 340. The sleeve opening 351 can be configured and sized to receive at least a portion of the cutting tool 500, such as the drill bit 502.

With reference to FIG. 5A, the second guide member 400 can guide the movement of the first cutting tool 500 or the second cutting tool 600 toward the first vertebral body V1 or the second vertebral body V2. The second guide member 400 can also serve to protect soft tissue while advancing a cutting tool, such as a drill bit, toward the first vertebral body V1 or the second vertebral body V2. In the depicted embodiment, the second guide member 400 can include a first guide sleeve 404, a second guide sleeve 406, and a second guide member body 402 connected between the first guide sleeve 404 and the second guide sleeve 406. The second guide member 400 can be constructed as a drill guide. Thus, the guide member body 402 can be a drill guide body. The first guide sleeve 404 and the second guide sleeve 406 can each be configured as a drill guide sleeve. The guide sleeves 404 and 406 can each define an internal diameter that is larger than the internal diameter of the guide sleeves 304 and 306. In an embodiment, the guide sleeves are drill sleeves. Thus, the drill sleeves 404 and 406 can each define an internal diameter that is larger than the internal diameter of the drill sleeves 304 and 306.

With continuing reference to FIG. 5A, the second guide member body 402 can be configured as a connecting member capable of interconnecting the first guide sleeve 404 and the second guide sleeve 406. In the depicted embodiment, the second guide member body 402 can be constructed as a bar, and can be elongate along a longitudinal direction 410. Furthermore, the second guide member body 402 can have a substantially planar configuration. However, it is envisioned that the second guide member 402 can alternatively have other suitable configurations. The second guide member body 402 can include a first end 412 and a second end 413 that is spaced from the first end 412 along the longitudinal direction 410.

With continuing reference to FIG. 5A, the second guide member 400 can further include a first attachment member 414, such as a flange, that protrudes from the first end of the second guide member body 402, and a second attachment member 416, such as a flange, that protrudes from the second end 413. The first attachment member 414 can be configured to attach the second the first guide sleeve 404 to the second guide member body 402, and can protrude from the second guide member body 402 at an oblique angle relative to the longitudinal direction 410. The second attachment member 416 can be configured to attach the second guide sleeve 406 to the second guide member body 402, and can protrude from the second guide member body 402 at an oblique angle relative to the longitudinal direction 410.

With continuing reference to FIG. 5A, the first guide sleeve 404 can include a first guide sleeve body 428. The first guide sleeve 428 can have a substantially cylindrical shape, and can define a first end 424 and a second end 426 opposite to the first end 424. The first end 424 can be spaced from the second end 426 along a first angled direction 430 that is oriented at an oblique angle relative to the longitudinal direction 410. The second guide sleeve body 428 can define an outer surface 418 that extends from the first end 424 to the second end 426. The outer surface 418 can be substantially smooth. The first guide sleeve 404 can further include one or more teeth 438 that protrude from the first guide sleeve body 428 in a direction away from the first end 424. The teeth can specifically protrude from the second end 426 of the first guide sleeve body 428, and can be configured to engage, such as penetrate, the first vertebral body or the second vertebral body V2 to fix the position of the first guide sleeve 404 relative to either the first vertebral body V1 or the second vertebral body V2. The first guide sleeve 404 can be referred to as a drill sleeve. Accordingly, the drill sleeve 404 can be configured and sized to be at least partially inserted in the first portion 246 of the guide hole 202 (FIG. 3C) or in the first portion 268 of the second guide hole 204. The drill sleeve 404 can be sized greater than the second portion 248 and the second portion 270 (FIG. 3C).

With continuing reference to FIG. 5A, the second guide sleeve 406 can include a second guide sleeve body 440. The second guide sleeve body 440 can have a substantially cylindrical shape, and can define a first end 442 and a second end 444 opposite to the first end 442. The first end 442 can be spaced from the second end 444 along a second angled direction 446. The second guide sleeve body 440 can further define an outer surface 448. The outer surface 448 can extend from the first end 442 to the second end 444. The second guide sleeve 406 can further include one or more teeth 456 that protrude from the second guide sleeve body 440 in a direction away from the first end 442. The teeth 456 can be elongate along the second angled direction 346. In the depicted embodiment, the teeth 456 can specifically protrude from the second end 444 of the second guide sleeve 406, and can be configured to engage, such as penetrate, the first vertebral body V1 or the second vertebral body V2 to fix the position of the second guide sleeve 406 relative to either the first vertebral body V1 or the second vertebral body V2. The second guide sleeve 406 can be referred to as a drill sleeve. Accordingly, the drill sleeve 406 can be configured and sized to be at least partially inserted in the first portion 246 of the guide hole. 202 (FIG. 3C) or in the first portion 268 of the second guide hole 204. The drill sleeve 406 can be sized greater than the second portion 248 and the second portion 270 (FIG. 3C).

With reference to FIG. 5B, the first guide sleeve body 428 can further define an inner surface 419 opposite to the outer surface 418. The inner surface 419 can define a first guide sleeve opening 421 that is elongate along the first angled direction 430. The first guide sleeve opening 421 can extend along a direction from the first end 424 toward the second end 426. In the depicted embodiment, the first guide sleeve opening 421 can define a first open end 423 and a second open end 425 in order to allow at least a portion of the first cutting tool 500 (FIG. 1A) or the second cutting tool 600 (FIG. 1A) to be inserted through the first guide sleeve body 428. The first open end 423 can be spaced from the second open end 425 along the first angled direction 430.

With continuing reference to FIG. 5B, the second guide sleeve body 440 can further define an inner surface 449 opposite to the outer surface 448. The inner surface 449 can define a second guide sleeve opening 451 that is elongate along the second angled direction 446. The second guide sleeve opening 451 can extend along a direction from the first end 442 toward the second end 444. In the depicted embodiment, the second guide sleeve opening 451 can define a first open end 453 and a second open end 455 in order to allow at least a portion of the first cutting tool 500 (FIG. 1A) or the second cutting tool 600 (FIG. 1A) to be inserted through the second guide sleeve body 440.

With reference to FIG. 6, the first cutting tool 500 can be configured to cut, such as drill, into a suitable tissue body, such as the first vertebral body V1 or the second vertebral body V2. The first cutting tool 500 is configured and sized to be at least partially received in any of the guide sleeve openings 321, 351, 421, or 451 such that the first cutting tool 500 can be coupled to the corresponding first guide member 300 or the second guide member 400. In the depicted embodiment, the first cutting tool 500 can be constructed as the first drill bit 502 that is configured to drill into a tissue body, such as the first vertebral body V1 or the second vertebral body V2. The first drill bit 502 can include a drill bit body 504, such as a shaft or a shank. The drill bit body 504 can be elongate along a longitudinal direction 506 and defines a drilling portion 508. Furthermore, the drill bit body 504 can define a first end 510 and a second end 512 opposite to the first end 510. The first end 510 can be spaced from the second end 512 along the longitudinal direction 506. The drill bit body 504 can define a cross-sectional dimension that can change along the longitudinal direction 506. For example, the drilling portion 508 can be tapered so that the cross-sectional dimension of the drill bit body 504 along the drilling portion 508 can increase in a direction from the second end 512 toward the first end 510.

With continuing reference to FIG. 6, the drilling portion 508 can define one more flutes 514 that extend into drill bit body 504. In the depicted embodiment, the flute 514 can extend along the longitudinal direction 506 in a helical pattern. The drilling portion 508 can be located closer to the second end 512 than to the first end 510, and can be configured to drill into a tissue body, such as the first vertebral body V1 or the second vertebral body V2. In addition to the drilling portion 508, the drill bit body 504 can include an attachment member 516, such as a tang, that is configured to attach the first drill bit 502 to a drill or any other device capable of rotating the first drill bit 502. When the first drill bit 502 is attached to a drill, the drill can rotate the first drill bit 502. The first drill bit 502 can further include a stop member 518 disposed on the drill bit body 504. The stop member 518 can also be referred to as the first stop member. The stop member 518 can be configured to abut at least a portion of the first guide member 300 or the second guide member 400 to limit the advancement of the first drill bit 502 along the appropriate guide sleeve opening (i.e., guide sleeve opening 321, 351, 421, or 451). In the depicted embodiment, the stop member 518 can be located closer to the first end 510 than to the second end 512, and can be configured as shoulder 519 disposed around an entire cross-section perimeter of a portion of the drill bit body 504. The cross-sectional dimension of the stop member 518 can be larger than the cross-sectional dimension of one or more of the guide sleeve openings (i.e., guide sleeve opening 321, 351, 421, or 451) such that the advancement of the first drill bit 502 through the guide sleeve opening can be stopped, or at least hindered, when the stop member 518 contacts a portion of the first guide member 300 or the second guide member 400 located adjacent the corresponding first open end (323, 353, 423, or 453).

With reference to FIG. 7, the second cutting tool 600 can be configured to cut, such as drill, in a suitable tissue body, such as the first vertebral body V1 or the second vertebral body V2. The second cutting tool 600 can be configured and sized to be at least partially received in any of the of the guide sleeve openings 321, 351, 421, or 451 such that the second cutting tool 600 can be coupled to the corresponding first guide member 300 or the second guide member 400. In the depicted embodiment, the second cutting tool 600 can be constructed as the second drill bit 602 that is configured to drill into a tissue body, such as the first vertebral body V1 or the second vertebral body V2. The drill bit 602 can include a drill bit body 604, such as a shaft or a shank. The drill bit body 604 can be elongate along a longitudinal direction 606 and defines a drilling portion 608. Furthermore, the drill bit body 604 can define a first end 610 and a second end 612 opposite to the first end 610. The first end 610 can be spaced from the second end 612 along the longitudinal direction 606. The drill bit body 504 can define a cross-sectional dimension. In particular, the drilling portion 608 can define a cross-sectional dimension that is smaller than the cross-sectional dimension of one or more of the guide sleeve openings 321, 351, 421, or 451 such that the drilling portion 608 can be inserted through the corresponding the guide sleeve opening 321, 351, 421, or 451. The drilling portion 608 can define one or more flutes 614 that extend into the drill bit body 604. In the depicted embodiment, the flute 614 can extend along the longitudinal direction in a helical pattern. The drilling portion can be located closer to the second end 612 than to the first end 610, and can be configured to drill into a tissue body, such as the first vertebral body V1 or the second vertebral body V2. The stop member 518 allows deeper advancement of the first drill bit 502 into the vertebral body than the advancement allowed by the second stop member 618 of the second drill bit 602 into the vertebral body.

The drill bit 602 can further include an attachment member 616 that is configured to attach the drill bit 602 to a drill or any other device capable of rotating the drill bit 602. When the drill bit 602 is attached to a drill, the drill can rotate the drill bit 602. The drill bit 602 can further include a stop member 618 disposed on the drill bit body 604. The stop member 618 can also be referred to as the second stop member. The stop member 618 can be configured to abut at least a portion of the first guide member 300 or the second guide member 400 to limit the advancement of the drill bit 602 along the appropriate guide sleeve opening (i.e., guide sleeve opening 321, 351, 421, or 451). The cross-sectional dimension of the stop member 618 can be larger than the cross-sectional dimension of one or more of the guide sleeve openings (i.e., guide sleeve opening 321, 351, 421, or 451) such that the advancement of the drill bit 602 through the guide sleeve opening can be stopped, or at least hindered, when the stop member 518 contacts a portion of the first guide member 300 or the second guide member 400 located adjacent the corresponding first open end (323, 353, 423, or 453). In the depicted embodiment, the stop member 618 can be located closer to the second end 612 than to the first end 610 such that, when the stop member 618 contacts a portion of the first guide member 300 or the second guide member 400, the drilling portion 608 can only advance the same depth as the third cutting tool 800, such as the chisel 802 (FIG. 1G), is capable of advancing into the first vertebral body V1 of the second vertebral body V2.

With reference to FIG. 8, the guide sleeve 306 (or 304) can define the first stop member 316 (or 314). The second stop member 518 of the drill bit 502 can be configured to contact the first stop member 316 (or 314) so as to define a cut depth D1 that is less than the insertion depth H (FIG. 1G) of the third cutting tool 800. The cut depth D1 can be defined by the length of a portion of the drill bit 502, such as the drilling portion 508, that extends beyond the guide sleeve 306 (or 304) when the first stop member 316 contacts the second stop member 518. The drill bit 502 defines the stop member 518 that is configured to abut the complementary stop member 314 supported by the guide portion 208 (FIG. 3A) so as to limit the movement of the drill bit 502 through the guide hole 202 or 204 along the guide hole axis 203 or 205 (FIG. 3B), such that the drill bit 502 defines a maximum cut depth D1 that is less than that of the drill bit 602. The drill bit 502 can be configured to be guided along drill guide sleeve 306 (or 304). The maximum cut depth D1 can be greater than a thickness of the cortical wall of the vertebral body V1 or V2 (FIG. 1A).

With reference to FIG. 9, the guide sleeve 406 (or 404) can define the first stop member 416 (or 414). The second stop member 618 of the drill bit 602 can be configured to contact the first stop member 416 (or 414) so as to define a cut depth D2 that is substantially equal to the insertion depth H (FIG. 1G) of the third cutting tool 800. The cut depth D2 can be greater than the cut depth D1. The cut depth D2 can be defined by the length of a portion of the drill bit 602, such as the drilling portion 608, that extends beyond the guide sleeve 406 (or 404) when the first stop member 416 (or 414) contacts the second stop member 618.

Figure 10A:
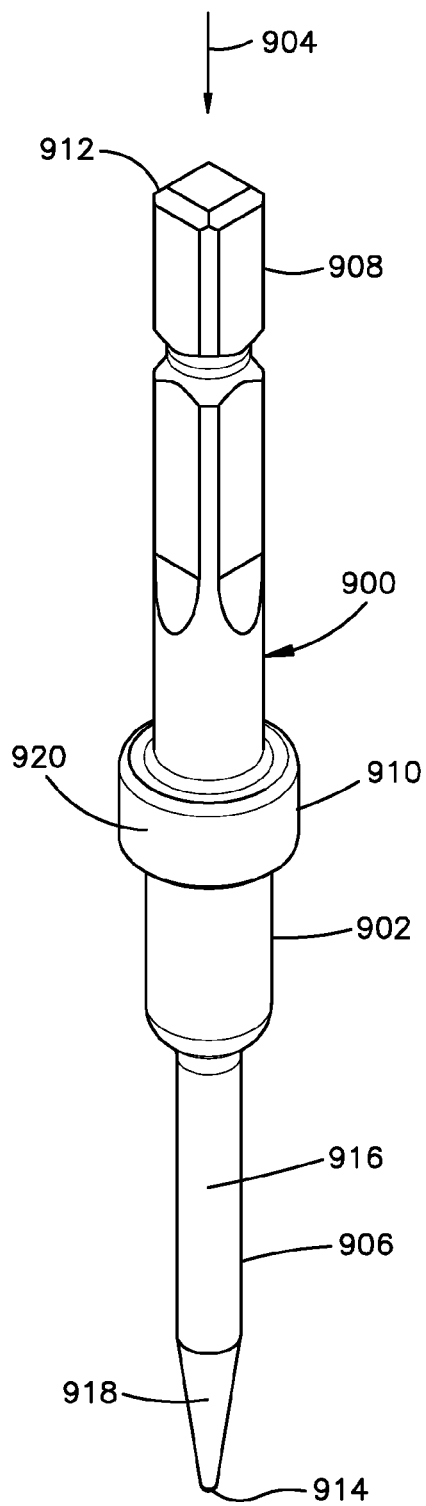
FIG. 10A is a perspective view of a bone anchor of the surgical cutting system shown in FIG. 1A.

With reference to FIG. 10A, a bone anchor 900 can be configured to be inserted into a tissue body, such as the first vertebral body V1 or the second vertebral body V2 and coupled to the cutting guide 200 to fix the position of the cutting guide 200 with respect to the first vertebral body V1 or the second vertebral body V2. In the depicted embodiment, the bone anchor 900 can include a bone anchor body 902 that is elongate along a longitudinal direction 904. The bone anchor body 902 can define a first end 912 and a second end 914 opposite to the first end 912. The first end 912 can be spaced from the second end along the longitudinal direction 904. The bone anchor body 902 can include an anchoring portion 906, an attachment portion 908, and a stop member 910 connected between the anchoring portion 906 and the attachment portion 908.

With continuing reference to FIG. 10A, the attachment portion 908 can be located closer to the first end 912 than to the first end 914, and can be configured to be attached to a handle to allow the bone anchor 900 to be advanced through a guide sleeve, such as guide holes 202 or 204, and into a tissue body, such as the first vertebral body V1 or second vertebral body V2. The bone anchor 900 can be advanced through a guide sleeve that is already coupled to the cutting guide 200 and into the first vertebral body V1 or second vertebral body V2 to fix the position of the cutting guide 200 relative the corresponding vertebral body.

With continuing reference to FIG. 10A, the anchoring portion 906 can be configured to penetrate a tissue body, such as the first vertebral body V1 and the second vertebral body V2, in order to fix the position of the bone anchor 900 relative to the tissue body. In the depicted embodiment, the anchoring portion 906 can include an anchoring portion body 916 that is elongate along the longitudinal direction 904. The anchoring portion body 916 can have a substantially cylindrical shape. In addition to the anchoring portion body 916, the anchoring portion 906 can include an anchoring tip 918 that is configured to be inserted into a tissue body, such as the first vertebral body V1 and the second vertebral body V1. The anchoring tip 918 can be tapered, such as pointed, such that the cross-sectional dimension of the tip 918 decreases in the longitudinal direction. For example, the anchoring tip 918 can have a substantially conical shape.

With continuing reference to FIG. 10A, as discussed above, a stop member 910 can be connected between the anchoring portion 906 and the attachment portion 908. The stop member 910 can be configured to abut at least a portion of the first guide member 300 or the second guide member 400 to limit the advancement of the bone anchor 900 along the appropriate guide sleeve opening (i.e., guide sleeve opening 321, 351, 421, or 451). In the depicted embodiment, the stop member 910 can be configured as an annular member 920 disposed around an entire cross-section perimeter of a portion of the bone anchor body 902. The cross-sectional dimension, such as the diameter, of the stop member 910 can be larger than the cross-sectional dimensions 252 or 274 of the guide holes 202 or 204, the such that the advancement of the bone anchor 900 through the guide hole can be stopped, or at least hindered, when the stop member 910 contacts a portion of the cutting guide 200. Consequently, the mechanical interference between the stop member 910 and at least a portion of the portion of the cutting guide 200 causes the bone anchor 910 to stop advancing toward the first vertebral body V1 or the second vertebral body V2, thereby limiting the insertion depth of the bone anchor 900 into the first vertebral body V1 or the second vertebral body V2.

Figure 10B:
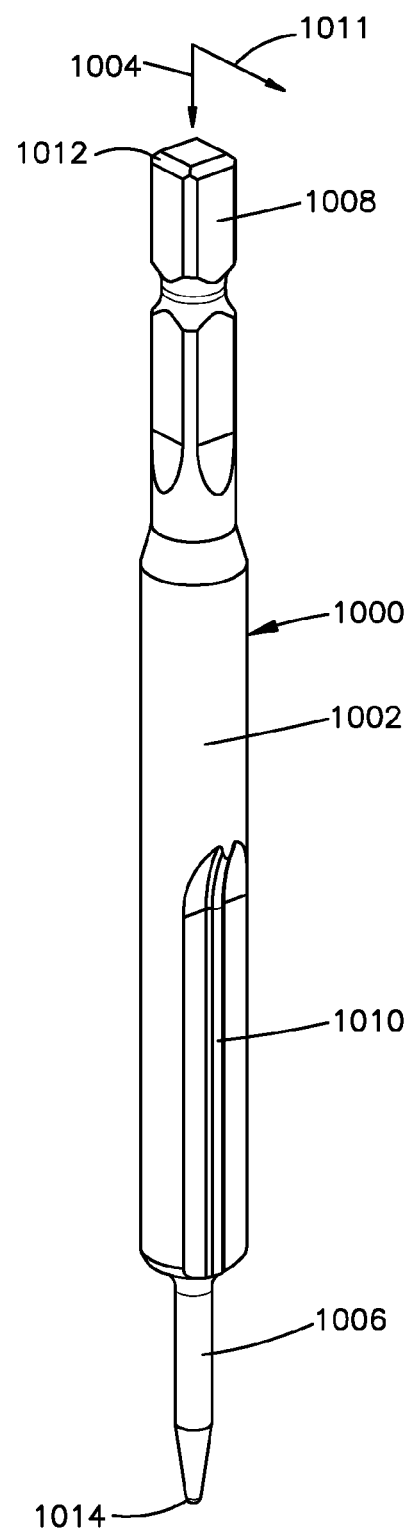
FIG. 10B is a perspective view of another bone anchor of the surgical cutting system shown in FIG. 1A.

With reference to FIG. 10B, a bone anchor 1000 can be configured to be inserted into a tissue body, such as the first vertebral body V1 or the second vertebral body V2, and coupled to the cutting guide 200 to fix the position of the cutting guide 200 with respect to the first vertebral body V1 or the second vertebral body V2. In the depicted embodiment, the bone anchor 1000 can include a bone anchor body 1002 that is elongate along a longitudinal direction 1004. The bone anchor body 1002 can define a first end 1012 and a second end 1014 opposite to the first end 1012. The first end 1012 can be spaced from the second end along the longitudinal direction 1004. The bone anchor body 1002 can include an anchoring portion 1006, an attachment portion 1008, and at least one engagement member 1010 connected between the anchoring portion 906 and the attachment portion 908.

With continuing reference to FIG. 10B, the attachment portion 1008 can be located closer to the first end 1012 than to the first end 1014, and can be configured to be attached to a handle to allow the bone anchor 1000 to be advanced through a guide sleeve, such as guide holes 202 or 204, and into a tissue body, such as the first vertebral body V1 or second vertebral body V2. The bone anchor 1000 can be advanced through a guide sleeve that is already coupled to the cutting guide 200 and into the first vertebral body V1 or second vertebral body V2 to fix the position of the cutting guide 200 relative the corresponding vertebral body.

With continuing reference to FIG. 10B, the bone anchor 1000 includes at least one engagement member 1010, such as a protrusion, that extends from the body bone anchor body 1002. In an embodiment, the engagement member 1010 extends from the bone anchor body 1002 in a lateral direction 1011 that is substantially perpendicular to the longitudinal direction 1004. In one embodiment, the bone anchor 1000 includes a pair of engagement members 1010 disposed on opposite sides of the bone anchor body 1002. The engagement members 1010 can be elongate along the longitudinal direction 1011. The engagement members 1010 are configured to mate with the engagement members 256 or 278 (FIG. 3C) so as to couple the cutting guide 200, such as the drill guide, to the bone anchor 1000.

Figure 11:
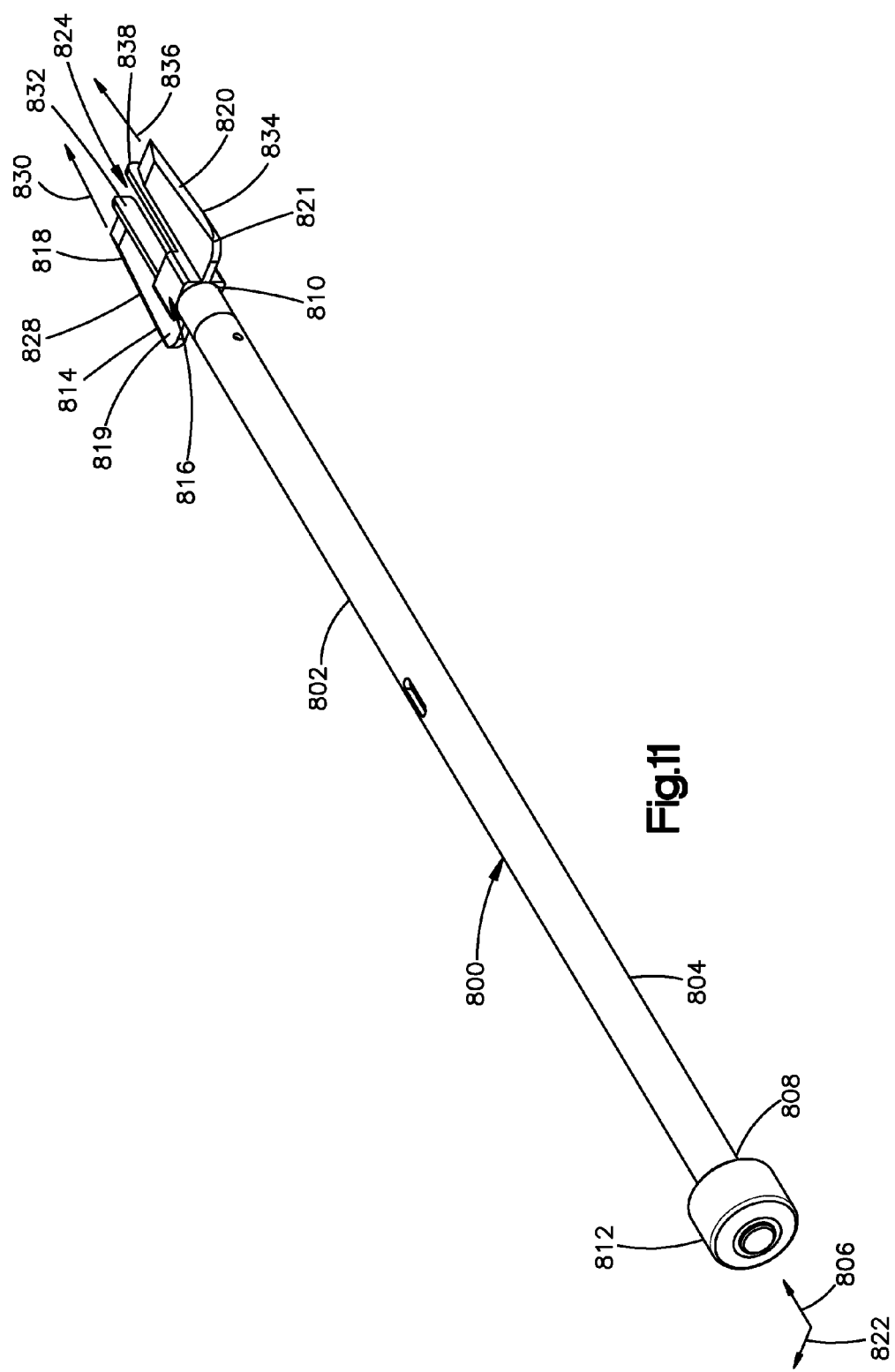
FIG. 11 is a perspective view of the third cutting tool shown in FIG. 1G.

With reference to FIG. 11, the third cutting tool 800 can be configured to be advanced into the first vertebral body V1 and the second vertebral body V1 to create the first aperture 9 (FIG. 1H) in the first vertebral body V1 and the second aperture 11 (FIG. 1H) in the second vertebral body V2. The first aperture 9 and the second aperture 11 are each configured and sized to receive at least one keel 702 of the intervertebral implant 700 (FIG. 1H). The third cutting tool 800 can be constructed as the chisel 802 or any other suitable tool capable of cutting a tissue body, such as the first vertebral body V1 or the second vertebral body V2. Examples of suitable chisels are described and illustrated in U.S. Pat. No. 7,491,204 issued on Feb. 17, 2009, the entire disclosure of which is herein incorporated by reference. In the depicted embodiment, the third cutting tool 800 can include a third cutting tool body 804 that is elongate along a longitudinal direction 806. The third cutting tool body 804 can define a first end 808 and a second end 810 opposite to the first end 808. The first end 808 can be spaced from the second end 810 along the longitudinal direction 806. The third cutting tool body 804 can be substantially cylindrical; however, the cutting tool body 804 can have other suitable shapes as desired.

With continuing reference to FIG. 11, the third cutting tool 800 can further include a handle 812 that is configured to be held by a user. The handle 812 can be coupled to the third cutting tool body 804. Specifically, the handle 812 can be coupled at the first end 808 of the third cutting tool body 804. In the depicted embodiment, the handle 812 can have a substantially circular cross-section. However, it is envisioned that the handle 812 can have any suitable shape as desired.

With continuing reference to FIG. 11, the third cutting tool 800 can further include a cutting portion 814 that is coupled to the third cutting tool body 804. The cutting portion 814 can be configured to be inserted into the first vertebral body V1 and the second vertebral body V2 to make the first aperture 9 (FIG. 1H) and the second aperture 11 (FIG. 1H). In the depicted embodiment, the cutting portion 814 can include a cutting portion body 816 that can be directly or indirectly connected to the third cutting tool body 804. In addition, the cutting portion 816 can include a first cutting arm 818 and a second cutting arm 820 each coupled to the cutting proton body 804.

With continuing reference to FIG. 11, each of the first cutting arm 818 and the second cutting arm 820 can protrude from the cutting portion body 816. The first cutting arm 818 and the second cutting arm 820 can each be elongate along the longitudinal direction 806. Moreover, the first cutting arm 818 and the second cutting arm 820 can be oriented substantially parallel to each other, and can have a substantially planar configuration. The second cutting arm 820 can be spaced from the first cutting arm 818 along a transverse direction 822 that is substantially perpendicular to the longitudinal direction 806. The first cutting arm 820 and the second cutting arm 822 can cooperate to define a gap 824 between them. The gap 824 can be configured and sized to receive at least a portion of the trial disc implant 100 (FIG. 2). In particular, the gap 824 can be configured and sized to receive at least a portion of the trial spacer member 102 (FIG. 2).

With continuing reference to FIG. 11, the first cutting arm 818 can include a first cutting arm body 819 that defines a first outer cutting edge 828 that can be elongate along a first angled direction 830. The first outer cutting edge 282 can also be referred as the first upper cutting edge. The first angled direction 830 can be oriented at an acute angle relative to the longitudinal direction 806. The first cutting arm body 819 can further include a first base 832 opposite to the upper cutting edge 828. The first base 832 can be elongated along the longitudinal direction 806, and can be configured and sized to be slidably received in the first groove 128 or the second groove 130 of the trial disc implant 100 (FIG. 2). Furthermore, the first base 832 can be spaced from the first outer cutting edge 828 along the transverse direction 822.

With continuing reference to FIG. 11, the second cutting arm 820 can include a second cutting arm body 821 that defines a second outer cutting edge 834 that can be elongate along a second angled direction 836. The second angled direction 836 can be oriented at an acute angle relative to the longitudinal direction 806. The second cutting arm body 821 can further include a second base 838 opposite to the second outer cutting edge 834. The second base 838 can be elongate along the longitudinal direction 806, and can be configured and sized to be slidably received in the first groove 128 or the second groove 130 of the trial disc implant 100 (FIG. 2). Furthermore, the second base 838 can be spaced from the second outer cutting edge 834 along the transverse direction 822.

FIGS. 12A-12E illustrates a method of creating the first aperture 9 and the second aperture 11 in the first vertebral body V1 and the second vertebral body V2 (FIG. 1H). As seen in FIG. 12A, a portion of the trial disc implant 100 is disposed in an intervertebral space S between the first vertebral body V1 and the second vertebral body V2. In particular, at least a portion of the trial spacer member 102 can be positioned in the intervertebral space S between the first vertebral body V1 and the second vertebral body V1. As discussed above, the trial spacer member 102 can be placed in the intervertebral space S to determine the appropriate implant footprint, lordotic angle, and disc height of the intervertebral implant 700 (FIG. 1H). The surgical system 10 can include a plurality of trial disc implants 100 having spacer members 102 of different sizes and shapes. As shown in FIG. 12E, the first guide member 300 can be angled relative to the vertebral body (V1 or V2) when it is coupled to the cutting guide 200 and the first guide sleeve 304 is disposed in one of the guide holes 202, 204 of the cutting guide 200. Moreover, the first guide sleeve 304 can be configured and sized to slide within the guide hole 202 or 204.

With reference to FIG. 12B, after the appropriate trial spacer member 102 has been partially disposed in the intervertebral space S, the cutting guide 200 can be coupled to the trial disc implant 100. To couple the cutting guide 200 to the trial disc implant 100, at least a portion of the cutting guide 200 can be positioned over at least a portion of the trial support member 104 such that the trial support member 104 is disposed in the cutting guide opening 282 (FIG. 3B) of the cutting guide 200. Accordingly, the cutting guide opening 282 can be configured and sized to receive at least a portion of the trial support member 104. The cutting guide 200 can be advanced toward the intervertebral space S such that at least a portion of the cutting guide body 206 (FIG. 3A) moves relative to the trial support member 104 toward the intervertebral space S. In particular, the cutting guide 200 can be moved relative to the trial disc implant 100 in a direction toward the intervertebral space S until the abutting member 280 (FIG. 3A) contacts at least a portion of the trial spacer member 102. At this juncture, the spacer members 284, 286 can contact the upper surface 116 (FIG. 2) and the lower surface 118 (FIG. 2) of the trial spacer member 102. The cutting guide 200 can be oriented relative to the first vertebral body V1 and the second vertebral body V2 so that the first guide hole 202 (FIG. 3C) defines a path toward the first vertebral body V1 and the second guide hole 204 defines a path toward the second vertebral body V2. Alternatively, the cutting guide 200 can be oriented relative to the first vertebral body V1 and the second vertebral body V2 so that the first guide hole 202 defines a path toward the second vertebral body V2 and the second guide hole 204 defines a path toward the first vertebral body V1.

With reference FIG. 12C, the first guide member 300 can be inserted through the first guide hole 202 or the second guide hole 204, and then advanced toward the first vertebral body V1 or the second vertebral body V2. In particular, the first guide sleeve 304 can be inserted through the first guide hole 202 or the second guide hole 204 and then advanced toward the first vertebral body V1 or the second vertebral body V2. Specifically, the first guide sleeve 304 can be inserted through the middle portion 248 (FIG. 3C) of the first guide hole 202 or the middle portion 270 (FIG. 3C) of the second guide hole 204 such that the mating feature 332 (FIG. 4A) of the first guide sleeve 304 mates with the mating feature 255 or 277 of the cutting guide 200, thereby fixing the first guide member 300 relative to the cutting guide 200. In the depicted embodiment, the engagement members 256 or 278 (FIG. 3C) can mate with the engagement members 336 (FIG. 4A) to lock the first guide member 300 relative the cutting guide 200. The first cutting tool 500, such as the first drill bit 502, can be inserted through the first guide sleeve opening 321 (FIG. 4B) of the first guide sleeve 304, and advanced toward the first vertebral body V1 or the second vertebral body V2. The first cutting tool 500 can be advanced into the first vertebral body V1 or the second vertebral body V2 to fix the first cutting tool 500, the first guide member 300, and the cutting guide 200 to the corresponding vertebral body. The bone anchor 900 can be inserted through the first guide sleeve opening 321 in lieu of the first cutting tool 300 to anchor the cutting guide 200 to the vertebral body.

With reference to FIG. 12D, a force can be applied to the cutting guide 200 in the direction indicated by arrow F to drive the trial spacer member 102 farther into the intervertebral space S, thereby further securing the trial disc implant 100 and the cutting guide 200 relative to the patient's spinal column.

With reference to FIG. 12E, the first guide sleeve 404 of the second guide member 400 can be inserted through the guide hole 202 or 204 (FIG. 3C) that is not receiving the first guide sleeve 304 of the first guide member 300. Specifically, the first guide sleeve 404 can be disposed in the first end portion 246 (FIG. 3C) of the first guide hole 202 or the first end portion 268 (FIG. 3C) of the second guide hole 204. The first guide sleeve 404 can then be advanced toward the first vertebral body V1 or the second vertebral body V2. In the depicted embodiment, the first guide sleeve 404 can be advanced toward the first vertebral body V1 because the first guide sleeve 300 is anchored to the second vertebral body V2. The first guide sleeve 404 can be advanced toward the corresponding vertebral body until the teeth 438 (FIG. 5A) penetrate at least a portion of the vertebral body in order to secure the guide member 400 to that vertebral body. The second cutting tool 600, such as the drill bit 602, can then be inserted through the guide sleeve opening 421 (FIG. 5B) of the first guide sleeve 404, and then advanced toward the first vertebral body V1 or the second vertebral body V2. In the depicted embodiment, the second cutting tool 600 can be advanced toward the first vertebral body V1. In particular, the second cutting tool 600 can be advanced toward the first vertebral body V1 until the stop member 618 abuts the first end 424 of the second guide sleeve body 428, thereby limiting the advancement of the second cutting tool 600 into the first vertebral body V1. In particular, the stop member 618 limits the advancement of the second cutting tool 600 into the vertebral body (V1 or V2) such that the drilling portion 608 of the second cutting tool 600 can only advance substantially the same depth as depth the third cutting tool 800 can advanced into the vertebral body.

Figure 12F:
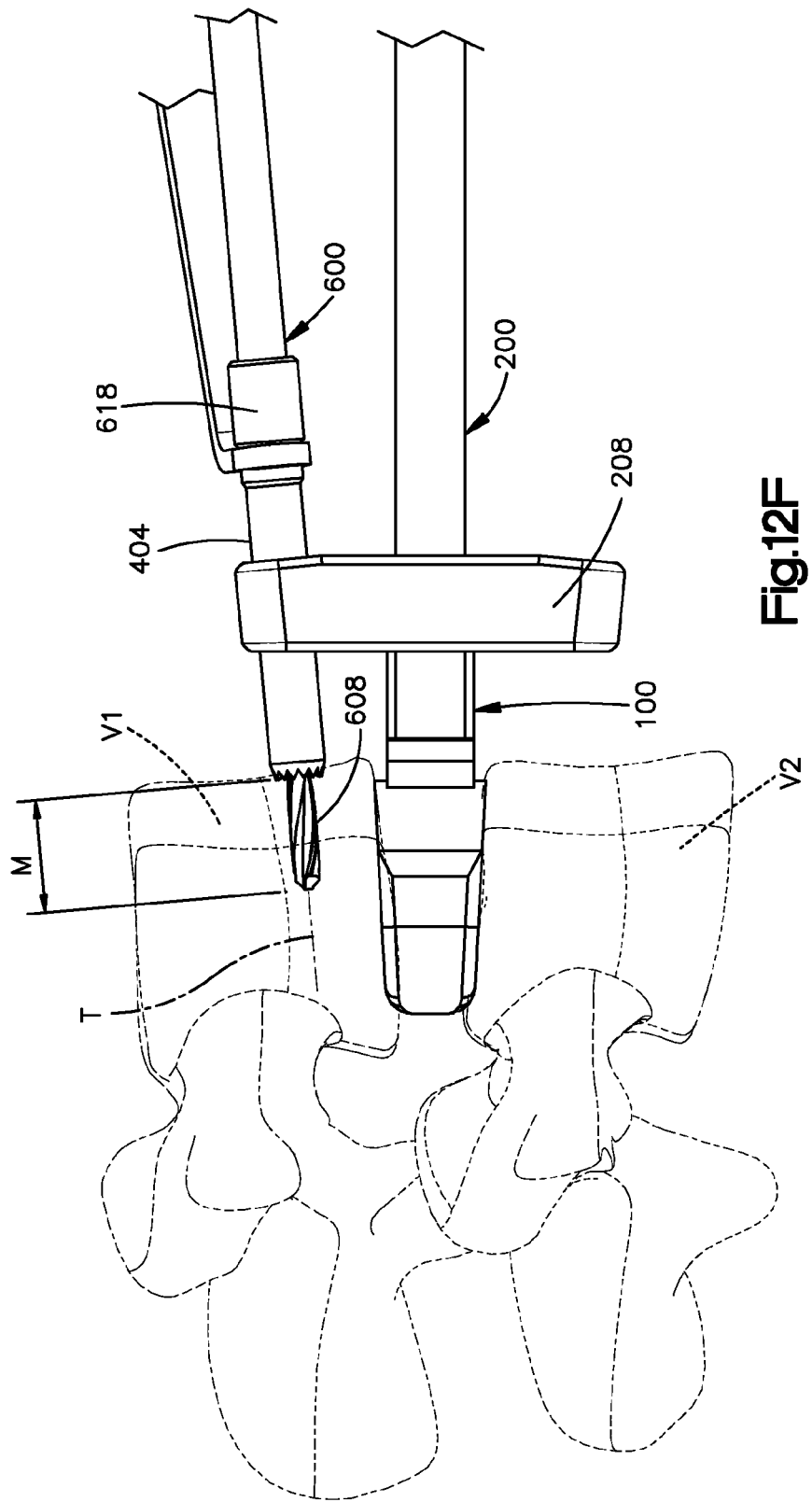
FIG. 12F is a side elevation view of the partial spinal column, the trial disc implant, the cutting guide, the second guide member, and the second cutting tool, and a superimposed image of the third cutting tool shown in FIG. 1A.

FIG. 12F illustrates at least a portion of the second cutting tool 600 inserted into the vertebral body V1 to a maximum cut depth M. In particular, the drilling portion 608 of the drill bit 602 can be inserted into the vertebral body V1 (or V2) to the maximum cut depth M.

The guide hole 202 (or 204) (shown in FIG. 1A) can be oriented relative to the trial implant 100 when the cutting guide 200 (e.g., drill guide) is coupled to the trial implant 100 such that the guide hole 202 (or 204) is configured to guide the drill bit 602 to advance through the guide hole 202 (or 204) along the guide hole axis 203 (or 205) (shown in FIG. 3B) into the vertebra body V1 (or V2) so as to create a drilled opening 1 (FIG. 2A) in the vertebral body. The drilled opening 1 (FIG. 2A) can be in substantial alignment with a cutting edge, such as the first outer cutting edge 828 second outer cutting edge 834, of the third cutting tool 800 (e.g., chisel 802) when the third cutting tool 800 is moved along the trial implant 100 and into the vertebral body. Thus, the path T of the drilling portion 608 into the vertebral body during operation substantially matches a trajectory P (FIG. 1G) of the outer cutting edge 828 (or outer cutting edge 834) when the third cutting tool 800 (e.g., chisel 802) is coupled to the trial disc implant 100 and advanced toward the vertebral bodies V1 and V2. The path T of the drilling portion 608 into the vertebral body (V1 or V2) substantially matches the trajectory of outer cutting edge 828 (or outer cutting edge 834) in order to create the first opening 1 (FIG. 1B). As discussed above, the first opening 1 can be created before forming the aperture 11 (or aperture 9) (FIG. 1H) in order to prevent, or at least inhibit, the formation of stress risers in the vertebral body (V1 or V2), thereby precluding, or at least hindering, the creation of stress cracks in the second vertebral body. In addition to opening 1, more openings 5 (FIG. 1E) can be created in the vertebral body by removing the second cutting tool 600 from the vertebral body, readjusting the position of the guide sleeve 404 relative to the guide hole (202 or 204), and then reinserting the cutting tool 600 through the guide sleeve 404 and into the vertebral body. The openings 5 (FIG. 1H) can be substantially parallel to the opening 1. The openings 5 can only extend into cortical portion of the vertebral body. After forming at least the opening 1 (FIG. 1H) in one vertebral body (V1 or V2), the process described above can be repeated to form the opening 1 in the other vertebral body. The opening 1 can be a drilled opening.

After creating at least one opening 1 in one vertebral body (V1 or V2), the first guide member 300 can be decoupled from the cutting guide 200, and the first cutting tool 500 can be removed the vertebral body and decoupled from the first guide member 300. The, second guide sleeve 306 can be inserted through one guide hole (202 or 204) of the cutting guide 200, and then advanced toward one vertebral body (V1 or V2) until the teeth 356 penetrate into at least a portion of the vertebral body. The second guide sleeve 306 can define a cross-sectional dimension, such as a diameter, that is configured and sized such the that second guide sleeve 306 can slide either the first guide hole 202 or the second guide hole 204 in the transverse direction 220 (FIG. 3A). The first cutting tool 500 can be inserted through the first guide sleeve opening 321 (FIG. 4B) of the second guide sleeve 306, and advanced into the vertebral body (V1 or V2). The first cutting tool 500 can then be slid along the guide hole (202 or 204) in the transverse direction 220 to create the aperture 9 or 11 (FIG. 1H) in the vertebral body V1. The method described above can be repeated to create a drilled opening 1 in the other vertebral body V2.

As described above, the present disclosure also relates to a method of making a drilled opening in a vertebral body. In an embodiment, the method can include the all or some of the following steps:

a) positioning a trial spacer member 102 in an intervertebral space between first and second vertebral bodies;

b) coupling a cutting guide 200, such as a drill guide, to the trial spacer member;
c) coupling a first guide sleeve 304, such as a drill guide sleeve, to the cutting guide 200;
d) inserting a first cutting tool 500, such as a drill bit 502, through the first guide sleeve 304 and into the second vertebral body to fix the position of the cutting guide 200 with respect to the first and second vertebral bodies;
e) coupling a second guide sleeve 404, such as a drill sleeve, to the cutting guide 200;
f) inserting a second cutting tool 600, such as a second drill bit 602, through the second guide sleeve 404 and into the first vertebral body to create a drilled opening 1;
g) repeating steps a-f to create a drilled opening in the second vertebral body;
h) removing the first cutting tool 500 from the first guide sleeve 304 and from the second vertebral body;
i) removing the second cutting tool 600 from the second guide sleeve 404 and from the first vertebral body;
j) decoupling the first guide sleeve 304 from the cutting guide 200;
k) decoupling the second guide sleeve 404 from the cutting guide 200;
l) leaving the trial spacer member in the intervertebral space between the first and second vertebral bodies;
m) advancing a third cutting tool 800, such as a chisel 802, along trial spacer member 102 to create apertures 9 that are sized to receive the keels 702 of an intervertebral implant 700.
n) removing the trial spacer member 102 from the intervertebral space;
o) positioning the intervertebral implant 700 in the intervertebral space such that keels 702 are received in the apertures 9.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed is:

1. A surgical cutting system comprising:
a drill guide including a guide portion having a guide portion body defining first and second longitudinal ends spaced from one another along a longitudinal direction, and first and second transverse ends that extend between the first and second longitudinal ends and are spaced from one another along a transverse direction that is substantially perpendicular to the longitudinal direction, the drill guide further including an attachment member between the first and second transverse ends and configured to couple the drill guide to a trial implant, the drill guide defining a guide hole that extends through the guide portion body along a guide hole axis from the first longitudinal end to the second longitudinal end, the guide hole defining first and second closed ends that are spaced from one another in the transverse direction, wherein the first and second closed ends are disposed between the first transverse end and the attachment member, and the guide hole is elongate from the first closed end to the second closed end in a plane that is perpendicular to the guide hole axis, the guide hole defining a first position, a second position, and at least one mating feature, the first and second positions spaced from one another along the transverse direction; a drill guide sleeve that is selectively receivable in the first position and the second position of the guide hole and that mates with the at least one mating feature so as to fix the drill guide sleeve in one of the first and second positions, the drill guide sleeve defining a sleeve body, a first stop member, and a sleeve opening that extends through the sleeve body; and
a drill bit configured to be at least partially received in the sleeve opening, the drill bit defining a second stop member that is configured to abut the first stop member so as to limit movement of the drill bit through the sleeve opening along the guide hole axis to a maximum cut depth when the drill bit is at least partially received in the sleeve opening and the drill guide sleeve is partially received in the guide hole,
wherein the guide hole is oriented relative to the trial implant when the drill guide is coupled to the trial implant such that the guide hole is configured to guide the drill bit to advance through the guide hole into a vertebral body so as to create a drilled opening in the vertebral body.

2. The surgical cutting system of 1, wherein the attachment member comprises a first spacer member and a second spacer member that is spaced from the first spacer member, the first and second spacer members are elongate along the longitudinal direction and protrude from the guide portion body along the longitudinal direction, the first and second spacer members are spaced from each other along the transverse direction, and the first and second spacer members are configured to engage corresponding first and second opposed surfaces of the trial implant.

3. The surgical cutting system of claim 2, wherein the guide hole axis is angularly offset with respect to the longitudinal direction, such that the drilled opening extends along a trajectory that is angularly offset with respect to the longitudinal direction.

4. The surgical cutting system of claim 3, wherein the drill guide further comprises an elongate drill guide body that extends from the guide portion body along the longitudinal direction.

5. The surgical cutting system of claim 4, wherein the guide portion body protrudes from the drill guide body along the transverse direction.

6. The surgical cutting system of claim 4, wherein the drill guide defines a drill guide opening that extends into the drill guide body, the drill guide opening configured to receive at least a portion of the trial implant such that insertion of the portion of the trial implant in the drill guide opening causes the drill guide to be coupled to the trial implant.

7. The surgical cutting system 6, wherein the drill guide opening is elongate along the longitudinal direction.

8. The surgical cutting system of claim 1, wherein the at least one mating feature includes a plurality of first engagement members that protrude into the guide hole, and the drill guide sleeve defines a plurality of second engagement members that are configured to mate with the plurality of first engagement members so as to couple the drill guide sleeve to the drill guide.

9. The surgical cutting system of claim 8, wherein the first engagement members are protrusions that protrude from the guide portion into the guide hole, and the second engagement members are splines defined along at least a length of the sleeve body, the splines configured to mate with the protrusions so as to couple the drill guide to the drill guide sleeve.

10. The surgical cutting system of claim 8, wherein:
the guide hole is defined by a first lateral end of the guide portion body and a second lateral end of the guide portion body, spaced from the first lateral end along a lateral direction perpendicular to the longitudinal and transverse directions; and
each of the first and second lateral ends defines a plurality of the mating features spaced apart from one another along the transverse direction.

11. The surgical cutting system of claim 1, wherein the guide hole defines a first portion and a second portion, wherein the first portion of the guide hole defines a lateral dimension greater than that of the second portion of the guide hole, the lateral dimension taken in a direction perpendicular to the longitudinal and transverse directions.

12. The surgical cutting system of claim 11, wherein the drill guide sleeve is sized to be inserted into the second portion.

13. The surgical cutting system of claim 12, wherein the drill guide sleeve is at least one first drill guide sleeve sized to be inserted into the second portion, and the surgical cutting system further comprises at least one second drill guide sleeve sized to be inserted into the first portion.

14. The surgical cutting system of claim 13, wherein the at least one second drill guide sleeve defines an internal diameter greater than that of the at least one first drill guide sleeve.

15. The surgical cutting system of claim 14, wherein the drill bit is a first drill bit, the surgical cutting system further comprising a second drill bit having a larger diameter than the first drill bit, the second drill bit sized to be guided through the at least one second drill guide sleeve.

16. The surgical cutting system of claim 15, wherein the at least one mating feature includes a plurality of first engagement members that at least partially define the guide hole.

17. The surgical cutting system of claim 1, comprising a second drill guide sleeve, which has a substantially smooth outer surface, and the drill guide sleeve defines a plurality of engagement members configured to interlock with the at least one mating feature of the guide portion.

18. The surgical cutting system of claim 17, wherein the second drill guide sleeve having the substantially smooth outer surface is configured to slide along the guide hole in the transverse direction without interlocking with the at least one mating feature.

19. The surgical cutting system of claim 18, wherein the second drill guide sleeve having the substantially smooth outer surface defines an outer diameter sized less than a cross-sectional dimension of the guide hole as measured at the at least one mating feature.

20. The surgical cutting system of claim 1, wherein the at least one mating feature is a protrusion that protrudes into the guide hole.

21. The surgical cutting system of claim 1, wherein the drill guide defines a second guide hole spaced from the guide hole along the transverse direction, wherein the second guide hole extends through the guide portion body along a second guide hole axis from the first longitudinal end to the second longitudinal end and the second guide hole is elongate in the transverse direction.

22. The surgical cutting system of claim 1, wherein the drilled opening is elongate along a drill axis that is substantially parallel to at least a portion of an upper surface or a lower surface of the trial implant.

23. The surgical cutting system of claim 1, further comprising the trial implant that is configured to be received in an intervertebral space between adjacent vertebral bodies, the trial implant having first and second vertebral body engaging surfaces that are spaced from one another along the transverse direction and are each configured to engage an endplate of one of the adjacent vertebral bodies.

24. The surgical cutting system of claim 23, wherein the trial implant has an attachment member configured to engage the attachment feature of the drill guide so as to removeably couple the drill guide to the trial implant such that the first and second closed ends of the guide hole are spaced along the transverse direction.

25. The surgical cutting system of claim 24, wherein the attachment feature of the trail implant includes a rod, and the attachment member of the drill guide includes a cutting guide opening configured to receive the rod.

* * * * *